(12) United States Patent
Appelbaum

(10) Patent No.: US 11,938,306 B2
(45) Date of Patent: Mar. 26, 2024

(54) GENERATING A DOSING AID LABEL FOR A SYRINGE

(71) Applicant: Nicholas Appelbaum, Green Point (ZA)

(72) Inventor: Nicholas Appelbaum, Green Point (ZA)

(73) Assignee: Nicholas Appelbaum, Geen Point (ZA)

( * ) Notice: Subject to any disclaimer, the term of this patent is extended or adjusted under 35 U.S.C. 154(b) by 1541 days.

(21) Appl. No.: 15/781,381

(22) PCT Filed: Jan. 18, 2017

(86) PCT No.: PCT/IB2017/050258
§ 371 (c)(1),
(2) Date: Jun. 4, 2018

(87) PCT Pub. No.: WO2017/125859
PCT Pub. Date: Jul. 27, 2017

(65) Prior Publication Data
US 2020/0261655 A1    Aug. 20, 2020

(30) Foreign Application Priority Data
Jan. 20, 2016   (ZA) ................................. 2016/00430

(51) Int. Cl.
*A61M 5/315*       (2006.01)
*A61M 5/31*        (2006.01)
(Continued)

(52) U.S. Cl.
CPC ........... *A61M 5/31535* (2013.01); *B65C 9/46* (2013.01); *B65D 25/36* (2013.01); *G09F 3/02* (2013.01);
(Continued)

(58) Field of Classification Search
CPC ...... A61M 5/31535; A61M 2005/3126; A61M 2205/6009; A61M 2205/6072;
(Continued)

(56) References Cited

U.S. PATENT DOCUMENTS 7,207,152 B2 * 4/2007 Baldwin ................. A61M 5/28
53/250
9,440,760 B2   9/2016 Srnka et al.
(Continued)

FOREIGN PATENT DOCUMENTS

| JP | 2008272162 A | 11/2008 |
| WO | 2013082423 A1 | 6/2013 |
| WO | 2013116353 A1 | 8/2013 |

OTHER PUBLICATIONS

International Search Report and Written Opinion for PCT/IB2017/050258, dated Sep. 20, 2017, 9 pages.
(Continued)

*Primary Examiner* — Thien M Le
*Assistant Examiner* — Asifa Habib
(74) *Attorney, Agent, or Firm* — Hoffman Warnick LLC

(57) ABSTRACT

A system and method for generating a dosing aid label for a syringe are described. In a method, patient information and medicament information are received. The medicament information includes one or more of a description of the medicament, a recommended dosage of the medicament and concentration information relating to the medicament. A dosing aid associated with the patient information and medicament information is generated. The dosing aid includes dosing information which is usable in guiding administration of a dose of the medicament. A print instruction message is transmitted to a printing device. The instruction message is configured to instruct the printing device to print a dosing aid label including the dosing aid on the syringe or a sheet of material configured to be affixed to a
(Continued)

syringe. The dosing aid label is usable in guiding administration of the dose of the medicament to the patient.

18 Claims, 10 Drawing Sheets

(51) Int. Cl.
*B65C 9/46* (2006.01)
*B65C 11/00* (2006.01)
*B65D 25/36* (2006.01)
*G06K 1/12* (2006.01)
*G09F 3/02* (2006.01)
*G16H 10/60* (2018.01)
*G16H 20/13* (2018.01)
*G16H 20/17* (2018.01)

(52) U.S. Cl.
CPC ............ *G16H 10/60* (2018.01); *G16H 20/13* (2018.01); *G16H 20/17* (2018.01); *A61M 2005/3126* (2013.01); *A61M 2205/6009* (2013.01); *A61M 2205/6072* (2013.01); *B65C 11/00* (2013.01); *G06K 1/121* (2013.01); *G09F 2003/0202* (2013.01)

(58) Field of Classification Search
CPC . A61M 5/00; B65C 9/46; B65C 11/00; B65D 25/36; B65D 2203/02; B65D 2501/24878; G09F 3/02; G09F 2003/0202; G09F 3/00; G16H 10/60; G16H 20/13; G16H 20/17; G06K 1/121
See application file for complete search history.

(56) References Cited

U.S. PATENT DOCUMENTS

| | | | |
|---|---|---|---|
| 9,867,947 B2* | 1/2018 | Appelbaum | A61M 5/31525 |
| 11,357,926 B2* | 6/2022 | Larsen | A61M 5/3157 |
| 2002/0017784 A1* | 2/2002 | Merry | G09F 3/0288 |
| | | | 283/81 |
| 2002/0173875 A1* | 11/2002 | Wallace | G16H 10/60 |
| | | | 700/242 |
| 2003/0216831 A1* | 11/2003 | Hart | G16H 15/00 |
| | | | 700/235 |
| 2004/0024368 A1* | 2/2004 | Broselow | A61M 5/31525 |
| | | | 604/207 |
| 2007/0204497 A1* | 9/2007 | de la Huerga | B65C 9/46 |
| | | | 283/67 |
| 2008/0097787 A1* | 4/2008 | Palazzolo | G09F 3/0288 |
| | | | 705/2 |
| 2008/0131362 A1* | 6/2008 | Rousso | A61M 5/1782 |
| | | | 424/1.11 |
| 2008/0314978 A1* | 12/2008 | Fedorko | G16H 70/40 |
| | | | 235/385 |
| 2009/0139126 A1* | 6/2009 | Alipour | G09F 3/0289 |
| | | | 40/642.02 |
| 2009/0294521 A1* | 12/2009 | de la Huerga | A61J 1/035 |
| | | | 235/375 |
| 2010/0174180 A1* | 7/2010 | Rousso | G16H 30/40 |
| | | | 600/431 |
| 2011/0093279 A1* | 4/2011 | Levine | G06F 16/24 |
| | | | 235/375 |
| 2012/0006712 A1* | 1/2012 | Kaplan | B65D 51/002 |
| | | | 220/592.2 |
| 2012/0241043 A1* | 9/2012 | Perazzo | A61J 7/0053 |
| | | | 141/2 |
| 2013/0238352 A1* | 9/2013 | Tussey | G16H 10/60 |
| | | | 705/2 |
| 2014/0130909 A1* | 5/2014 | Dudar | B42D 15/00 |
| | | | 137/551 |
| 2014/0157731 A1* | 6/2014 | Perazzo | B65B 3/003 |
| | | | 141/2 |
| 2014/0207079 A1* | 7/2014 | Creaturo | A61M 5/3129 |
| | | | 604/207 |
| 2014/0263614 A1 | 9/2014 | Keefe et al. | |
| 2016/0001003 A1* | 1/2016 | Perazzo | A61M 5/1782 |
| | | | 53/493 |
| 2016/0055317 A1* | 2/2016 | Levine | G06K 7/10297 |
| | | | 705/2 |
| 2016/0092744 A1* | 3/2016 | Keefe | G06V 30/2247 |
| | | | 382/183 |
| 2016/0166776 A1* | 6/2016 | Appelbaum | A61M 5/1412 |
| | | | 604/189 |
| 2016/0318311 A1 | 11/2016 | Edwards et al. | |
| 2017/0028130 A1* | 2/2017 | Perazzo | B67B 3/2006 |
| 2018/0002056 A1* | 1/2018 | Enos | G06F 17/40 |
| 2020/0254186 A1* | 8/2020 | Hernandez | A61M 5/31595 |
| 2021/0343388 A1* | 11/2021 | Brown | G16H 40/67 |

OTHER PUBLICATIONS

MedKeeper, PharmacyKeeper, "The PharmacyKeeper solution provides web and mobile-based applications to Improve key pharmacy operational processes." 2019, http://www.medkeeper.com/products/.

Extended European Search Report for 17741161.8, dated Oct. 7, 2019, 12 pages.

Merry et al., "A new infusion syringe label system designed to reduce task complexity during drug preparation," Anaesthesia 62: 486-491 (2007).

* cited by examiner

GENERATING A DOSING AID LABEL FOR A SYRINGE

CROSS-REFERENCE TO RELATED APPLICATIONS

This application is the US national phase of PCT/IB2017/050258, filed 18 Jan. 2017, which claims priority from South African provisional patent application number 2016/00430 filed on 20 Jan. 2016, each of which is incorporated by reference herein.

FIELD OF THE INVENTION

This invention relates to generating a dosing aid label for a syringe, and in particular to a system and method for generating a dosing aid label.

BACKGROUND TO THE INVENTION

The preparation of medicaments for administration via a syringe can be a complex and hence error-prone practice. A healthcare professional preparing a medicament for administration via a syringe may need to consider various factors in determining an appropriate dosage of the medicament to be administered to a patient.

A common factor encountered is performing a weight-based dose calculation by converting a recommended weight-based dose of the medicament (usually expressed in milligrams per kilogram) into a required dose of the medicament (usually in milligrams). Having determined the required dose, the healthcare professional may need to perform a further volume calculation in order to determine the correct dose of medicament which must be drawn from a certain ampoule/medicament concentration (usually expressed in milligrams per milliliter). This second step may or may not require the use of an appropriate diluent.

In one particular example provided for the purpose of illustration, Etomidate is available in 20 mg/10 ml ampoules, while the required dose is 0.3 mg/kg of patient body weight. Further, syringes generally include simple graduations indicating volumes within the syringe in milliliters. This process is can be more complicated and prone to error in the field of pediatrics, for example.

A healthcare professional needing to administer Etomidate to a patient having body weight of, for example, 9 kg would need to determine the required dose, being 2.7 mg in this scenario, and then determine the volume of the Etomidate solution, being 1.35 ml, which must be drawn into and administered from the syringe. These calculations are required so that the healthcare professional can use the graduations provided on the syringe (indicating volumes in ml) to correctly administer the dose of the medicament (expressed in mg) for the patient's body weight.

In other examples, other factors may need to be considered; for example the medicament concentration may be expressed in units, as a ratio (e.g. 1:10,000) and so on. As a further complication, particularly in pediatrics, dilutions may need to be made in order to have realistically workable volumes to administer. Other complications, for example, include rate based medicament infusions (e.g. micrograms per kilogram per minute), doses which are titrated to effect, or the necessity to correct for physiological deviations (e.g. for creatinine clearance in the case of renal impairment).

It should be evident from the above that healthcare professionals may be required to perform calculations which can be quite complex. It is not uncommon for errors to be made while performing such calculations. These calculation errors occur most commonly in high pressure situations, but may still occur wherever medications are administered. It may also happen that the healthcare professional specifying the dosage of the medicament to be administered may not actually prepare the dose, instead asking another healthcare professional to do so, which can increase the occurrence of errors.

In some instances, administering an incorrect dosage of a medicament to a patient can have dire consequences.

The Applicant has attempted to address this problem by providing a label for a syringe. The label, disclosed in PCT Patent Publication No. WO 2015025300 A2, now granted as U.S. Pat. No. 9,867,947, includes a first scale visible from an operatively front surface of the label along a major edge thereof. The first scale is a volume indication scale calibrated to align with an existing volume indication scale on the syringe. The label also includes a second scale provided adjacent the volume indication scale. The second scale relates to a patient body weight scale calibrated so that a correct recommended dose of a medicament can be delivered to a patient of a given weight, either during administration of the medicament or during preparation of a mixture to be administered.

However, labels such as those described above are particular to a syringe having a specific caliber, and possibly capacity too. This is so because the volume indications on the label must align with the volume indications on the syringe in order to calibrate the second scale when the label is affixed to the syringe. Further, the label is particular to a specific medicament and recommended dosage of that medicament.

Due to the extensive variety of medicaments and syringes which may be available, and the extent to which dosages of medicaments can vary, such a label may have limited use in practice. It may, for example, be onerous if not impractical to stock labels for each type of syringe, each type of medicament and each dosage of the medicament. Even if all appropriate labels were stocked, it may be time consuming and tedious to locate an appropriate label, which may impair efficacy of the labels.

Accordingly, there remains scope for improvement.

The preceding discussion of the background to the invention is intended only to facilitate an understanding of the present invention. It should be appreciated that the discussion is not an acknowledgment or admission that any of the material referred to was part of the common general knowledge in the art as at the priority date of the application.

SUMMARY OF THE INVENTION

In accordance with the invention there is provided a computer-implemented method for generating a dosing aid label for a syringe, the method comprising: receiving patient information relating to a patient to whom a medicament is to be administered; receiving medicament information relating to a medicament to be administered to the patient, the medicament information including one or more of a description of the medicament, a recommended dosage of the medicament, and concentration information relating to the medicament; generating a dosing aid associated with the patient information and medicament information, the dosing aid including dosing information which is usable in guiding administration of a dose of the medicament; and, transmitting a print instruction message to a printing device, the instruction message being configured to instruct the printing device to print a dosing aid label including the dosing aid, the label being printed either on a syringe or on a sheet of material configured to be affixed to a syringe, such that the dosing aid label can be used to guide administration of the dose of the medicament to the patient.

Generating the dosing aid may include accessing a pre-generated dosing aid from a database or dynamically generating the dosing aid in near real-time.

Further features provide for the method to include: prompting a user for patient information relating to a patient to whom a medicament is to be administered; and, prompting a user for medicament information relating to a medicament to be administered to the patient.

A yet further feature provides for receiving medicament information relating to a medicament to be administered to include receiving the medicament information from one of an input device of the user interface device or a tag or barcode associated with the medicament.

A yet further feature provides for receiving medicament information relating to a medicament to be administered to include receiving a selection of a preconfigured regimen, the preconfigured regimen including a description of one or more medicaments, each of the one or more medicaments being associated with a recommended dosage of the medicament and a concentration of the medicament.

A further feature provides for receiving medicament information relating to the medicament to include obtaining the recommended dosage of the medicament and concentration information relating to the medicament from a medicament information database.

In one embodiment, generating the dosing aid includes generating a dosing scale, the dosing scale being associated with the patient information and medicament information and including at least one indication being arranged to translate a volume defined by a position of a stopper within a syringe into dosing information relating to a dose of the medicament to be administered to the patient, the dosing scale being calibrated based on the dosing scale operatively being located on the syringe in a predetermined position.

Further features provide for the method to include obtaining syringe type information relating to a type of syringe to be used to administer the medicament, the syringe type information at least including the type of syringe to be used and optionally marker information relating to one or more markers provided on a syringe of the type to be used; and for obtaining syringe type information to include one or more of: obtaining syringe type information from a database; obtaining syringe type information from a barcode associated with a syringe to be used; receiving user input including the syringe type information; receiving the syringe type information from calipers associated with the user interface device; and, determining an optimal type of syringe to be used based on one or both of the patient information and medicament information.

Still further features provide for generating a dosing scale to include generating a dosing scale associated with the patient information, medicament information and syringe type information, and for the dosing scale to be calibrated based on the scale operatively being located in a predetermined position relative to the one or more markers provided on the syringe of the type to be used.

Further features provide for the marker information to include a syringe volume indication scale corresponding to markers in the form of graduations provided on a syringe of the type to be used which indicate volumes within the syringe for transmitting the print instruction message to include transmitting a print instruction message configured to instruct the printing device to include the syringe volume indication scale on the sheet of material on which the label is printed; for the syringe volume indication scale to be included along a first major edge of the sheet of material and adjacent the dosing scale and for the syringe volume indication scale to be provided on the label for alignment with the graduations provided on the syringe of the type to be used for location of the dosing scale in the predetermined position on the syringe.

A yet further feature provides for the generated dosing scale to include one or more of the group of: a body weight scale, a dilution assistance scale, an adapted dilution scale, an infusion administration assistance table, a bolus dose scale, a physiological-variable adjusted scale, an ideal body weight conversion scale, a titrated to effect scale, and a multi-dose adjustment scale.

A further feature provides for generating the dosing scale to include calculating the dosing scale based on one or more of: the patient information, the medicament information, the syringe type information, dimensions of the dosing aid label, information relating to the predetermined position and information relating to the sheet of material.

In another embodiment, the dosing aid includes instructions for steps to be performed by a user in order to administer the dose of the medicament.

The invention extends to a dosing aid system for generating a dosing aid label for a syringe, the dosing aid system including a memory for storing computer-readable program code and a processor for executing the computer-readable program code, the system comprising: a patient information receiving component for receiving patient information relating to a patient to whom a medicament is to be administered; a medicament information receiving component for receiving medicament information relating to a medicament to be administered to the patient, the medicament information including one or more of a description of the medicament, a recommended dosage of the medicament, and concentration information relating to the medicament; a dosing aid generating component for generating a dosing aid associated with the patient information and medicament information, the dosing aid including dosing information which is usable in guiding administration of a dose of the medicament; and, a transmitting component for transmitting a print instruction message to a printing device, the instruction message being configured to instruct the printing device to print a dosing aid label including the dosing aid, the label being printed either on a syringe or on a sheet of material configured to be affixed to a syringe, such that the dosing aid label can be used to guide administration of the dose of the medicament to the patient.

The generating component may be configured to access a pre-generated dosing aid from a database or to dynamically generate the dosing aid in near real-time.

In one embodiment, the dosing aid is in the form of a dosing scale associated with the patient information and medicament information, the dosing scale including at least one indication being arranged to translate a volume defined by a position of a stopper within a syringe into dosing information relating to a dose of the medicament to be administered to the patient, the dosing scale being calibrated based on the scale operatively being located in a predetermined position on the syringe.

A further feature provides for the transmitting component to transmit a print instruction message configured to instruct the printing device to print the label on a sheet of material configured to be affixed to a syringe with the dosing scale in the predetermined position, such that the dosing scale can be used to guide administration of the dose of the medicament to the patient.

A yet further feature provides for the system to include a user interface device and the printing device, the printing device comprising: a receiving component for receiving the print instruction message; and, a printer for printing the label directly on a syringe or on a sheet of material configured to be affixed to a syringe.

A further feature provides for the system to include a syringe having one or more label markers provided thereon, the one or more label markers being arranged to cooperate with the dosing aid label including a dosing scale, the one or more label markers facilitating positioning of the dosing scale on the syringe in the predetermined position, such that operatively with the label affixed to the syringe with the dosing scale in the predetermined position, the dosing scale translates volumes within the syringe into dosing information thereby to guide administration of a dose of a medicament to a patient.

In another embodiment, the dosing aid includes instructions for steps to be performed by a user in order to administer the dose of the medicament.

The invention extends to a syringe for use with a dosing aid label, the syringe having one or more label markers provided thereon, the one or more label markers being arranged to cooperate with a dosing aid label including a dosing scale, the one or more label markers facilitating positioning of the dosing scale on the syringe in a predetermined position, such that operatively with the label affixed to the syringe with the dosing scale in the predetermined position, the dosing scale translates volumes within the syringe into dosing information thereby to guide administration of a dose of a medicament to a patient.

In one embodiment the one or more label markers include a formation on a barrel of the syringe. The formation may be a depression extending partially along a length of the barrel of the syringe and at least partially around the barrel, the depression defining a zone having a shape and size corresponding to that of the label such that affixing the label to the zone positions the dosing scale provided on the label in the predetermined position.

In another embodiment, the one or more label markers include guides printed or formed on the syringe and arranged so as to align with at least two edges of the label and to thereby facilitate positioning of the dosing scale in the predetermined position. The guides may include two parallel, spaced apart lines printed on a surface of a barrel of the syringe and extending circumferentially at least partially around the barrel, the lines being spaced apart so as to align with parallel minor edges of the rectangular label, such that affixing the label to the barrel of the syringe in-between the two lines positions the dosing scale provided on the label in a predetermined position relative to the lines.

Embodiments of the invention will now be described, by way of example only, with reference to the accompanying drawings.

DETAILED DESCRIPTION WITH REFERENCE TO THE DRAWINGS

Figure 1:
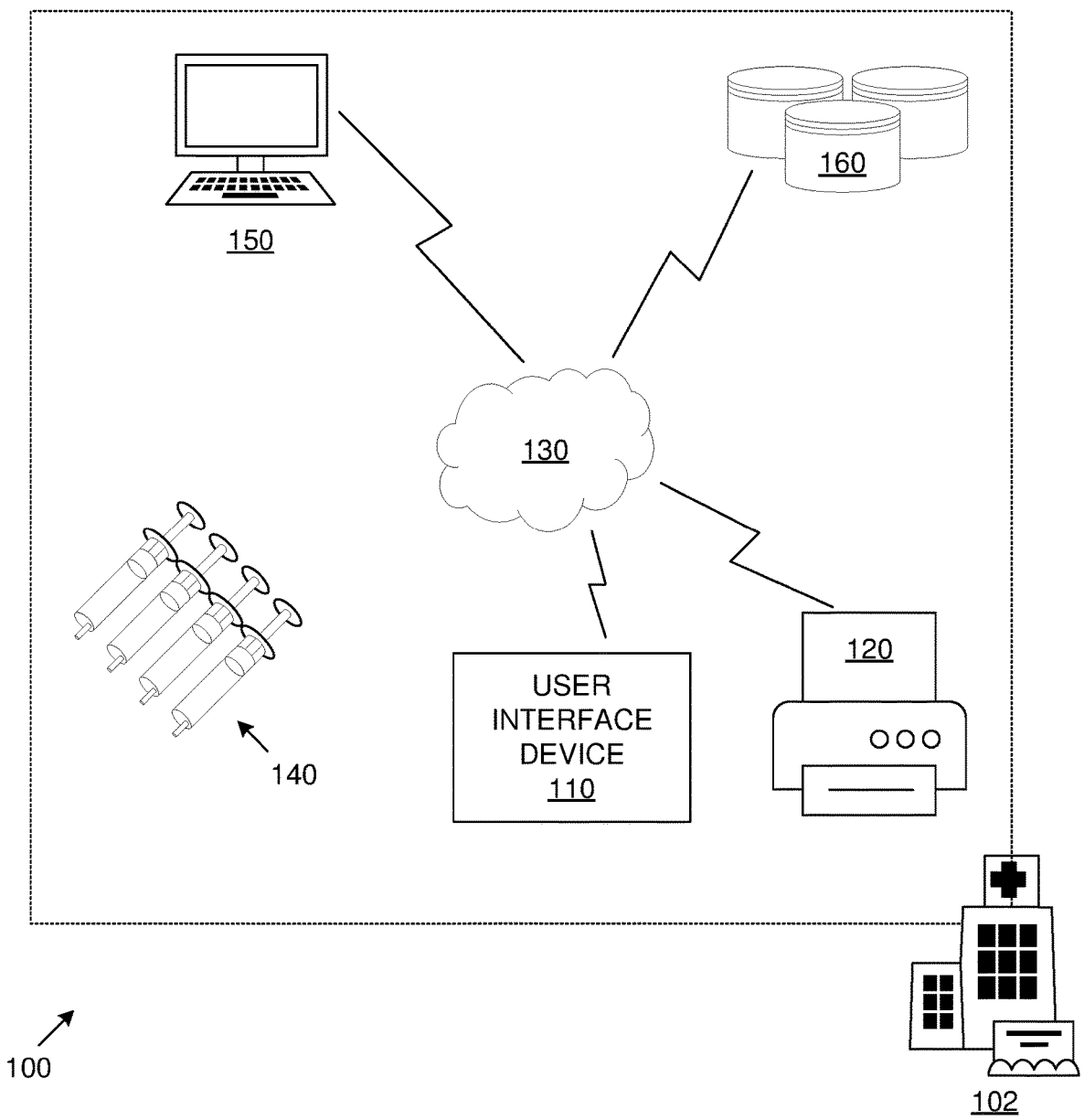
FIG. 1 is a schematic diagram which illustrates one exemplary embodiment of a dosing aid system for generating a dosing aid label.

Aspects of the disclosure are directed towards generating and printing a label that can be used to guide administration of a dose of a medicament to a patient. In some scenarios the label may be generated and printed by the healthcare professional (e.g. at point of care). An exemplary label may include two scales, one of which being a preparation scale (e.g. to aid dilution) and the other being an administration scale (to guide administration).

A system, method and syringe for providing dosing information are described herein. In the system and method, patient information and medicament information relating to a medicament to be administered to the patient are received. The medicament information may include a description of the medicament (e.g. the name of the medicament), a recommended dosage (for a particular indication of the medicament) of the medicament and concentration information. The concentration information may include information relating to the concentration in which the medicament is available (e.g. the concentration of an ampoule in mg/ml) and optionally a suggested final concentration of the medicament in cases where the medicament should be diluted.

A dosing aid is generated, which may be in the form of a dosing scale associated with the patient information and medicament information or in the form of instructions of steps to be performed by a user in order to administer a dose of the medicament. In the case of a dosing scale, at least one indication may be provided which is arranged to translate a volume defined by a position of a stopper within a syringe into dosing information relating to a dose of the medicament to be administered to the patient. The dosing scale is calibrated based on the scale operatively being located in a predetermined position on the syringe which is to be used to administer the medicament. A dosing aid label including the dosing scale is either printed on a syringe to be used or on a sheet of material configured to be affixed to the syringe. The dosing aid label is configured to be located on the syringe such that the label locates in the predetermined position. The dosing scale can then be used to guide preparation of the dose and/or administration of the dose of the medicament to the patient. The dosing scale accordingly provides a guide which indicates to a user the extent to which a stopper of the syringe must be drawn out in order to draw the required dose of medicament, or in the case of a full syringe, the extent to which the stopper must be plunged, in order to administer the correct dose.

As used herein, the predetermined position may be a position in which indications of the dosing scale are positioned correctly along a length of the barrel of the syringe such that a volume defined by a position of a stopper within the syringe when the stopper is aligned with an indication provided on the dosing scale is correctly translated into dosing information relating to a dose of the medicament to be administered to the patient. The predetermined position may therefore be dependent on (or a function of) one or more of the dimensions of the dosing aid label, the arrangement of the dosing scale (and optionally volume indication scale) on the dosing aid label and marker information, such as the positioning of the markers (or graduations) on the syringe.

Markers provided on the syringe are used to facilitate the positioning of the label on the syringe such that the dosing scale locates in the predetermined position. Edges of the label or positioning information provided on the label may align with the markers. The markers may either be in the form of volume-indicating graduations typically found on conventional syringes or in the form of label makers which cooperate with the label (or with positioning information provided on the label). For example, in one embodiment, the syringe may be a conventional syringe and the markers may be graduations provided on the syringe which are used to indicate volumes within the syringe. The positioning information provided on the label may be in the form of a volume indication scale which aligns with these graduations. In other embodiments described herein, the syringe may include label markers in the form of formations formed within the barrel wall or guides printed on the syringe and which are arranged to align with edges of the label (or with positioning information provided on the label).

FIG. 1 is a schematic diagram which illustrates one exemplary embodiment of a dosing aid system (100). The system (100) may be located at or at least accessible from a health facility (102) such as a hospital, clinic, surgery or the like. The system (100) includes a user interface device (110) and a printing device (120).

The user interface device (110) may be any appropriate electronic device capable of receiving input from a user, outputting information to a user and interacting with other components of the system. In some embodiments, the user interface device (110) may be a communication device, such as a mobile phone (e.g. a smart phone), a tablet computer, a personal digital assistant, a wearable electronic device and the like. In other embodiments, the user interface device (110) may be provided by a computing device such as a desktop or laptop computer. It is further anticipated that the user interface device (110) may be a user interface associated or integrated with the printing device (120). In some implementations therefore the user interface device (110) and printing device (120) may be a single, integrated device.

The user interface device (110) is in communication with the printing device (120) and is configured to send and receive data and/or messages to and from the printing device (120). The user interface device (110) may communicate with the printing device via a wired or wireless communication network or via a communication bus, as the case may be. The user interface device (110) may further be configured to access communication networks (130) such as a health facility intranet and/or the Internet.

The user interface device (110) may be configured to access various systems provided at the health facility, such as a pharmacy back-end (150), via the communication network (130). Accessing a pharmacy back-end (150) may enable medicament ordering functionality as well as for prefilling and pre-labelling of syringes to be done in a pharmacy associated with the health facility.

The user interface device (110) may further have access to one or more databases (160). The databases (160) may be maintained locally in the user interface device (110) or may be accessed remotely via the communication network (130). The databases (160) may include a patient information database in which patient information is stored; a stock information database, for example, indicating which syringes and medicaments are in stock; a medicament information (e.g. formulary) database in which medicament information such as a medicament description, dosing information, concentration information, treatment guidelines, and other information relating to various medicaments is stored; a dosing scale database for storing pre-generated dosing scales, and the like.

The printing device (120) includes a label printer configured to print labels on or for attachment to syringes (140). Labels may be printed on a generally rectangular sheet of flexible material. The material, which may be translucent, is capable of being affixed to a syringe and, for example, may be in the form of a sticker having an adhesive disposed on an operatively back surface thereof for this purpose. In other embodiments, the printing device includes a printer configured to print labels directly onto syringes.

The dosing aid system (100) is configured to receive patient information relating to a patient as well as a description of a medicament to be administered to the patient. The system (100) is configured to obtain medicament information relating to the medicament, such as a recommended dosage of the medicament, a concentration in which the medicament is provided (e.g. the concentration of the medicament in an ampoule) and a suggested final concentration of the medicament after dilution (if required). The system (100) may be further configured to obtain syringe type information relating to a type of syringe (140) to be used to administer the medicament. The syringe type information may include the type of syringe to be used and marker information relating to one or more markers provided on a syringe of the type to be used.

The system (100) is configured to generate a dosing aid, which may be in the form of a dosing scale, and which may be associated with the patient information, medicament information and optionally the syringe type information. The dosing scale includes at least one indication being arranged to translate a volume defined by a position of a stopper within a syringe (140) of the type to be used (when aligned with the indication) into dosing information relating to a dose of the medicament to be administered to the patient. The system (100) prints a dosing aid label including the dosing scale on a sheet of material which is configured for attachment to a syringe (140) of the type to be used such that, with the dosing scale in the predetermined position relative to the syringe, the dosing scale can be used to guide preparation and/or administration of the dose of the medicament to the patient. In other embodiments, the dosing aid label is printed directly on the syringe.

The system (100) accordingly allows for a patient-, medicament- and/or dose-specific label including dosing information to be generated and printed in near real-time at a health facility (102). By correctly affixing the label including the dosing scale to the syringe, a user administering the medicament may be visually guided by comparing the position of a stopper or plunger within the syringe to the dosing scale so as to administer the desired dose of the medicament. Such a dosing scale may alleviate the cognitive burden of performing complex calculations which may be experienced by the person administering the dose (e.g. having to convert a milligram per kilogram of patient body weight dose into milliliters of medicament solution to be drawn into and administered from the syringe).

Figure 2:
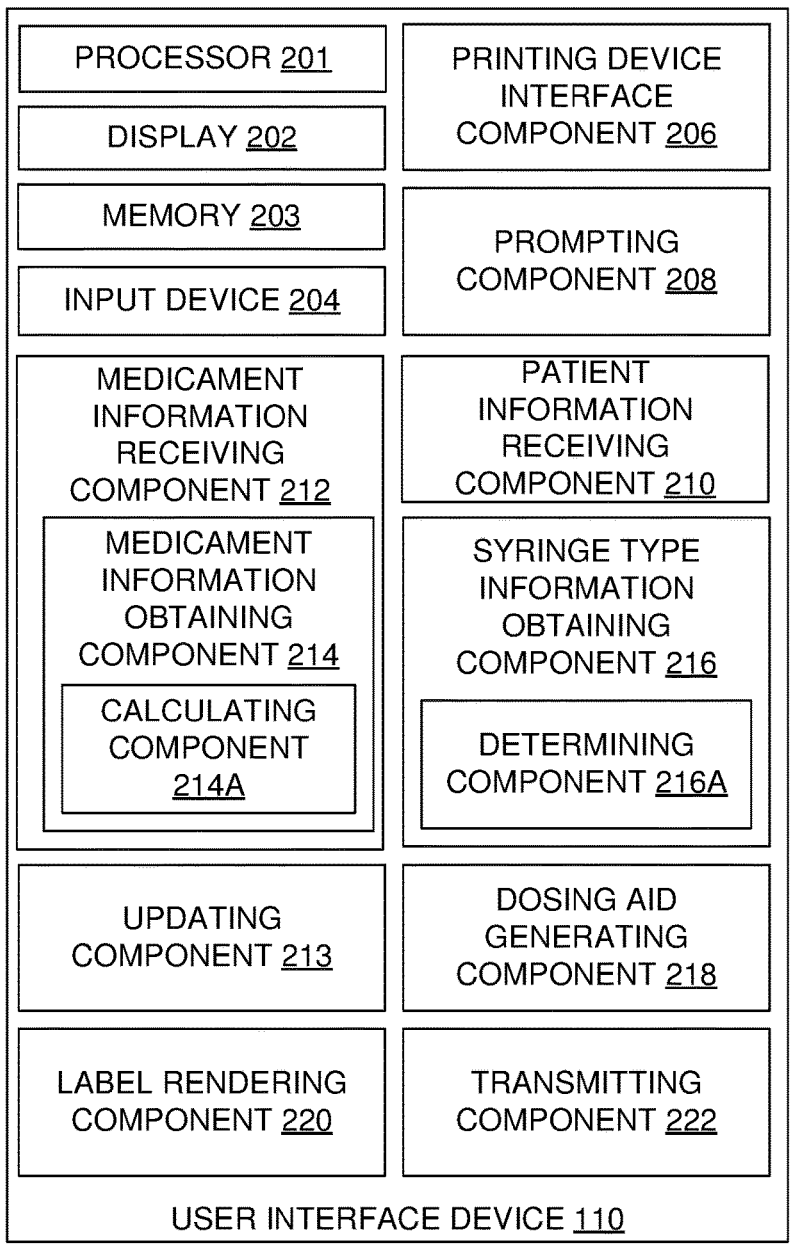
FIG. 2 is a block diagram which illustrates components of the dosing aid system illustrated in FIG. 1.
Figure 2:
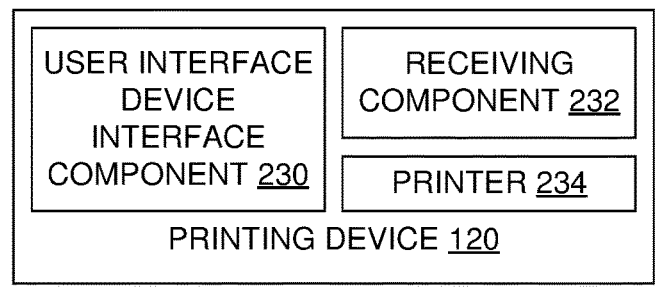

The system (100) described above will now be elaborated on with reference to FIG. 2, a block diagram which illustrates components of the system (100).

The user interface device (110) may include a processor (201) for executing the functions of components described below, which may be software units executing on the user interface device (110) either being resident thereon or provided remotely. Instructions, which may be stored in a memory component (203), may be provided to the processor (201) to carry out the functionality of the described components. Some or all of the components may be provided by a software application downloadable onto and executable on the user interface device. It should also be appreciated that, in other embodiments, some of the components described as being provided by the user interface device may be provided by the printing device or a remote server (e.g. in a cloud-based application).

The user interface device (110) includes a display (202) arranged to display information to a user and an input device (204) for receiving user input. The input device (204) may be provided by a keyboard. In some cases, the display (202) and input device (204) may be provided by a touch-sensitive display screen.

The user interface device (110) includes a printing device interface component (206) arranged to interface with the printing device (120). The printing device interface component (206) may provide the appropriate protocols for transmitting and receiving data and/or messages to and from the printing device (120) via the communication network (130) or communication bus, as the case may be.

The user interface device (110) includes a prompting component (208) arranged to prompt a user for input via the display (202). The prompting component (208) may prompt a user for patient information relating to a patient to whom a medicament is to be administered and for a description of a medicament to be administered to the patient. The prompting component (208) may further be arranged to prompt the user for syringe type information relating to a type of syringe to be used.

The user interface device (110) includes a patient information receiving component (210) arranged to receive patient information relating to a patient to whom a medicament is to be administered. The patient information may include one or more of the group of: a name of the patient, a unique identifier associated with the patient (e.g. an identifier used by the health facility to identify the patient), a total body weight of the patient, an ideal body weight of the patient, an estimated weight of the patient, a weight range in which a body weight of the patient falls, a gender of the patient, an age of the patient, physiological information relating to the patient, a condition with which the patient is suffering, and the like. In some implementations, some or all of the patient information may be stored in or obtainable via a tag associated with the patient (e.g. on a health facility-issued wristband, etc.).

The patient information receiving component (210) may be arranged to receive patient information via the input device (204). In other embodiments, the patient information receiving component (210) may receive a patient identifier (or other subset of patient information) input by a user and may query a patient information database for further information relating to the patient. It is also anticipated that in some embodiments, the patient information receiving component (210) may receive the patient information from, for example, a tag associated with the patient (e.g. via a barcode scanner or near field communication antenna) a weighing scale integrated into a bed in which the patient is lying or other such devices. The system may also be informed by a remote connection (via the network) to other hospital resources.

In some embodiments, the patient information receiving component (210) may be configured to receive user input in the form of a patient body weight or a patient body weight range. If that information is unavailable, the patient information receiving component (210) may receive user input in the form of a patient age and a patient gender. The patient information receiving component (210) may be arranged to determine an estimated patient weight using the received patient age and patient gender.

The user interface device (110) further includes a medicament information receiving component (212) which is configured to receive information relating to a medicament to be administered to the patient. The information may include a description of the medicament, such as the name, concentration, volume, expiry date, etc. and may be received via the input device (204).

In some embodiments, the medicament information receiving component (212) is configured to use the prompting component (208) to display a medicament menu. The medicament menu may provide two options. A first option may be an option to select one or more medicaments based on a preconfigured regimen. Each preconfigured regimen may be associated with one or more medicaments, and optionally dosages of the one or more medicaments. Exemplary preconfigured regimens may include (in an emergency department scenario), one or more rapid sequence intubation (RSI) regimens, or a regimen for a fitting child, and the like. A second option of the medicament menu may be an option to select specific medicaments individually. The medicament menu may arrange the medicaments in classifications; for example, in an anaesthetic-specific implementation, the medicaments may be classified into the following exemplary classifications: induction agents, opioids, sedatives, resuscitation, muscle relaxants and the like. The method of presenting medication menus may change depending on the setting in which the system is employed. The medicament menu may be configured to receive medicament selections as the user navigates through the menu and may update a list as the user selects medicaments.

In other embodiments, the medicament information receiving component (212) communicates with a barcode scanner, camera or radio frequency antenna associated with the user interface device (110) and is configured to receive the medicament description by scanning a tag associated with a medicament to be administered. Exemplary tags may be disposed on medicament packaging (such as an ampoule)

and may be in the form of a medicament label, a barcode (or other appropriate graphical code), a radio frequency tag or the like. In some embodiments, the medicament information receiving component (212) includes an optical character recognition (OCR) component for performing optical character recognition on text provided on the medicament label so as to receive the description of the medicament.

The medicament information receiving component (212) may include a medicament information obtaining component (214) which is arranged to obtain medicament information relating to the medicaments which are to be administered to the patient. The medicament information obtaining component (214) may query a database to obtain the medicament information associated with a particular medicament. In some embodiments, the medicament information is included in a tag (such as the medicament label) associated with the medicament and the medicament information obtaining component (214) obtains the information from the tag. It is further anticipated that in some embodiments, the medicament information is received together with the medicament description.

The medicament information may include a recommended dosage of the medicament and concentration information. The concentration information may include the concentration in which the medicament is available (e.g. concentration of an ampoule of the medicament in mg/ml) and a suggested final concentration of the medicament in the case that dilution is required before administration. The concentration information of the medicament may thus refer to the concentration of an ampoule of the medicament in, for example, milligrams (mg) per milliliter (ml). Alternatively, the concentration of the medicament may, in the case of a medicament provided in powder form, refer to a recommended reconstitution and dilution of the powder; for example, in milligrams per milliliter of diluent (mg/ml) or as a ratio (e.g. 1:10,000). The concentration information may further include dilution information indicating a recommended or proposed dilution of the medicament. The dilution information may include a type of diluent (e.g. water for injection, saline solution, 5% dextrose etc.).

The recommended dosage of the medicament may be a recommended dosage of the medicament in milligrams per kilogram of body weight of the patient, a recommended dosage of the medicament in micrograms which should be administered to the patient per minute (mcg/min) or the like. In some cases, the recommended dosing information may simply refer to an adult dose (e.g. X mg for an adult). It is further anticipated that the recommended dosage may be specific to a particular condition; for example in the case of adrenaline, the dose for a shocked patient would be less than the dose with a patient in cardiac arrest. In some cases, the recommended dosage may be associated with a preconfigured regimen selected by the user. In some embodiments, the medicament information obtaining component (214) may calculate and suggest a recommended dosage based on the patient information (e.g. weight, age, condition, etc.).

It is anticipated that in some embodiments, the medicament information obtaining component (214) includes a calculating component (214A) arranged to calculate at least a portion of the medicament information based on the patient information. For example, the calculating component (214A) may be configured to perform medicament metabolism correction (e.g. in the case of renal failure) to recommend a dose of the medicament based on the patient's metabolic condition.

It is anticipated that the user interface device (110) may include an updating component (213) configured to update various databases to which the user interface device has access. For example, the updating component (213) may update the patient information database to indicate that the patient will be administered the dose of the medicament. Further, the updating component (213) may update the stock information database to update syringe and medicament stock levels based on the syringe and medicament used. In some embodiments, the updating component (213) may be configured to update the medicament information database with current medical guidelines, to add and remove new or old medicaments, and the like.

In some embodiments, for example where various types of syringes are being used, the user interface device (110) may also include a syringe type information obtaining component (216) which is arranged to obtain syringe type information relating to a type of syringe to be used to administer the medicament. The syringe type information may include the type of syringe to be used (e.g. make, capacity, caliber, etc.) and marker information relating to one or more markers provided on the syringe of the type to be used. The marker information may include a syringe volume indication scale corresponding to graduations provided on a syringe of the type to be used which indicate volumes within the syringe. Alternatively, the marker information may include information relating to locations of one or more label markers provided on the syringe of the type to be used. The label markers may be in the form of formations or guides provided on the syringe and are arranged to facilitate positioning of a dosing scale in a predetermined position. In some cases the marker information may inform the size of label to be used and where on the label the dosing scale should be provided. In some cases the positioning of label markers may be standardised for a particular type of syringe and marker information may be inferred from the type of syringe being used. The syringe type information may further include the capacity of the syringe, the bore or caliber of the syringe, the length of the syringe and the like.

The syringe type information obtaining component (216) may include a determining component (216A) arranged to determine an optimal type of syringe to be used based on the patient information and medicament information. For example, the determining component (216A) may determine a capacity required in order to administer the recommended dose of the medicament and may recommend a syringe based on the required capacity. It is further anticipated that the syringe type information obtaining component (216) may query a stock information database to evaluate stock levels of syringes at the health facility and may also take into account financial implications in determining an optimal (or recommended) syringe. In other cases, the syringe type information obtaining component (216) may be configured to display a list of possible syringe types and to receive user input in the form of a selection of a type of syringe to be used. In some instances, the list of possible syringes is based on a preconfigured list of favorite syringes.

In some embodiments, the syringe type information obtaining component (216) may communicate with a caliper device associated with the user interface device and being arranged to determine the caliber of the syringe to be used. The caliper device may measure an internal or external diameter of a syringe to be used in order to determine the bore. The caliper may, for example, measure an external diameter of the syringe and then estimate an internal diameter based on an expected thickness of the syringe material. The syringe type information obtaining component (216) may then use the estimated internal diameter to determine an appropriate syringe volume scale. In other embodiments, the syringe type information obtaining component (216) may determine the caliber of the syringe based on user input received via the input device (204) (e.g. in the form of the distance between the 5 ml and 10 ml graduations on the syringe, etc.) by measuring the spacing between graduations provided on the syringe or, alternatively, by accessing a database, or by scanning a barcode printed on a syringe of the type to be used or the like.

The user interface device (110) includes a dosing aid generating component (218) for generating a dosing aid. In this embodiment, the dosing aid is in the form of a dosing scale which is calibrated based on the scale operatively being located in a predetermined position on a syringe of the type to be used and is associated with the patient information, the medicament information and optionally the syringe type information. The dosing scale may be patient specific and may include at least one indication which is arranged to translate a volume defined by a position of a stopper within a syringe of the type to be used into dosing information relating to a dose of the medicament to be administered to the patient. The dosing scale may for example be for a patient of a specific weight and for the administration of a specific medicament. The indication may be a line which defines a particular volume when the dosing scale is placed on the syringe in the predetermined position and when the stopper of the syringe aligned with the indication. The particular volume (expressed in ml) may be the volume required to administer a given quantity (expressed in mg) of the medicament having a particular concentration (expressed in mg/ml). The given quantity of the medicament is the weight of the medicament determined based on the weight of the patient and the recommended dosage expressed as milligrams per kilogram (mg/kg) (e.g. by multiplying the patient weight in kg by the recommended dosage in mg/kg). In other cases, the dosing scale may include a number of indications, for example, for administering a number of doses, for administering varying doses depending on the patient's condition, or for administering varying doses depending on the patient weight, etc.

Some exemplary patient-specific dosing scales include a bolus dose scale, an adapted dilution scale, a physiological-variable adjusted scale, an ideal body weight conversion scale, a titrated to effect scale, and a multi-dose adjustment scale. An example of a physiological-variable adjusted scale is a creatinine clearance specific scale which would, for example, allow for the patient's renal clearance to be factored in, for example by showing a smaller dose where the patient's kidneys are in a poor condition. An adapted dilution scale may be used together with a bolus dose scale and guides a user in preparing a syringe-full of medicament or medicament and diluent mixture with a fixed mg/kg concentration. In such cases, the total amount of medicament required is variable, depending on the weight of the patient, and this is indicated on the adapted dilution scale. An ideal body weight conversion scale may be used in cases where a patient is overweight, the ideal body weight reflecting the patient's ideal body weight and being the weight value on which the dose of the medicament should be based. Various labels including various exemplary dosing scales are described in greater detail below with reference to FIGS. 8A and 8B.

Just as a user would administer a medicament from a syringe based on the position of the stopper relative to the graduations provided on the syringe indicating volumes within the syringe, the dosing scale described herein enables a user to administer a dose of the medicament from a syringe based on the position of the stopper relative to indications provided on the dosing scale. When the dosing scale is in the predetermined position on the syringe, the indications translate the position of the stopper into dosing information, obviating the need for the user to perform complex calculations in order to administer the dose.

In other cases, the dosing scale may not be specific to a patient. Some examples of such dosing scales include those labels disclosed in PCT Patent Publication No. WO 2015025300 A2, now granted as U.S. Pat. No. 9,867,947, which is incorporated herein by reference for all purposes. Such labels include a patient body weight scale, a dilution assistance scale, an infusion administration assistance table and the like. An infusion administration assistance table will inform a user of the required rate of administration of the mixture in order to achieve a desired infusion dose, for example in micrograms per kilogram per minute (mcg/kg/min). This may be particularly useful where the equipment generally used for such procedures, such as computerised syringe pumps or syringe drivers, are not available, by introducing the mixture into a suitable vessel for infusion by a standard portable intravenous pump that electronically regulates and monitors the flow of intravenous fluid, or even simply gravity controlled dial-in flow meters. It should be appreciated that more than one assistance scale may be included on a single label.

In some embodiments, the dosing aid generating component (218) may generate a dosing scale based on the syringe type information, patient information and/or medicament information. Generating and printing a dosing aid label including a dosing aid in near-real time may enable patient specific dosing scales (e.g. specific to the patient's weight, condition and/or physiology) to be provided on syringes, lowering the cognitive burden experienced by healthcare professionals in administering medicament dosages.

The dosing scale generating component (218) may include a calculating component arranged to calculate the dosing scale based on one or more of: the patient information, the medicament information, the syringe type information, dimensions of the label, information relating to the predetermined position and information relating to the sheet of material. For example, for a given syringe volume and caliber, the dosing scale will require indications spaced at specific intervals in order to translate volumes within the syringe into dosing information and the calculating component may calculate the spacing of the indications and location information corresponding to a location on the label and/or syringe at which the dosing scale must be located. The calculating component may be configured to calculate the dosing scale and/or dosing information such that when the dosing scale is located in the predetermined position on the syringe of the type to be used, the dosing scale operates to translate volumes within the syringe into dosing information.

In another embodiment, the dosing aid includes instructions for steps to be performed by a user in order to administer the dose of the medicament. For example, the instructions may first instruct the user to draw a given volume from an ampoule of a medicament to be administered; to then draw a certain volume of diluent; and to then administer a certain volume from the syringe (e.g. in milliliters).

In other embodiments, the dosing aid generating component (218) may access a database in which a number of pre-generated dosing scales are stored, each of the pre-generated dosing scales being associated with one or more of syringe type information, patient information and medicament information. By querying the database with the syringe type information, patient information and/or medicament information, the dosing aid generating component (218) may access and retrieve an appropriate dosing scale.

The user interface device (110) may include a label rendering component (220) arranged to render a label for display to a user via the display (202). The label rendering component (220) may be configured to determine the dimensions of the label and to provide the dosing scale on the label in a particular position such that the label and markers provided on the syringe cooperate to locate the dosing scale on the syringe in the predetermined position, thus calibrating the system. The label rendering component (220) may be configured to provide additional information on the label. The additional information may include patient information, medicament information (for example expiry date) and syringe type information.

The user interface device (110) further includes a transmitting component (222) which is arranged transmit a print instruction message to the printing device (120) which instructs the printing device (120) to print the label. The transmitting component (222) may transmit a print instruction message including the label to the printing device (120) via the printing device interface component (206) to enable the printing device to print the label. In other embodiments, the print instruction message may include the dosing scale and optionally additional information or alternatively information pointing to the dosing scale and optionally additional information which is to be provided on the label. The print instruction message may instruct the printing device to render and print the label including the dosing scale and optionally additional information. In some embodiments, the print instruction message instructs the printing device to provide the syringe volume indication scale or other positioning information along a first major edge of the label and adjacent the dosing scale, the syringe volume indication scale being provided for alignment with the graduations provided on the syringe of the type to be used.

The printing device (120) may include a processor for executing the functions of the described components which may be software units executing on the printing device (120) either being resident thereon or provided remotely. Instructions may be provided to the processor to carry out the functionality of the described components.

The printing device (120) may include a user interface device interface component (230) arranged to interface with the user interface device (110). The user interface device interface component (230) provides the appropriate protocols for transmitting and receiving data and/or messages to and from the user interface device (110) via the communication network (130) or communication bus, as the case may be.

The printing device (120) may further include a receiving component (232) arranged to receive the print instruction message from the user interface device (110) via the user interface device interface component (230). The printing device (120) includes a printer (234) configured to print the label. In some embodiments, the printer (234) prints the label on an operatively front surface of a generally rectangular sheet of material. The label includes the dosing scale and the additional information. The additional information may include: patient information (e.g. patient name, patient body weight, etc.), medicament information (e.g. name of medicament, concentration, dose, etc.) and syringe type information, and positioning information (e.g. syringe volume indication scale) being arranged to facilitate positioning the dosing scale on the syringe in the predetermined position (e.g. using one or more markers, such as graduations provided on the syringe). In some embodiments, the print instruction message instructs the printer to render and print the label, the message including the dosing scale and optionally additional information or alternatively pointers to the dosing scale and additional information to be used. In another embodiment, the printer prints the dosing aid label directly on a syringe which will be used to administer the medicament.

Figure 3:
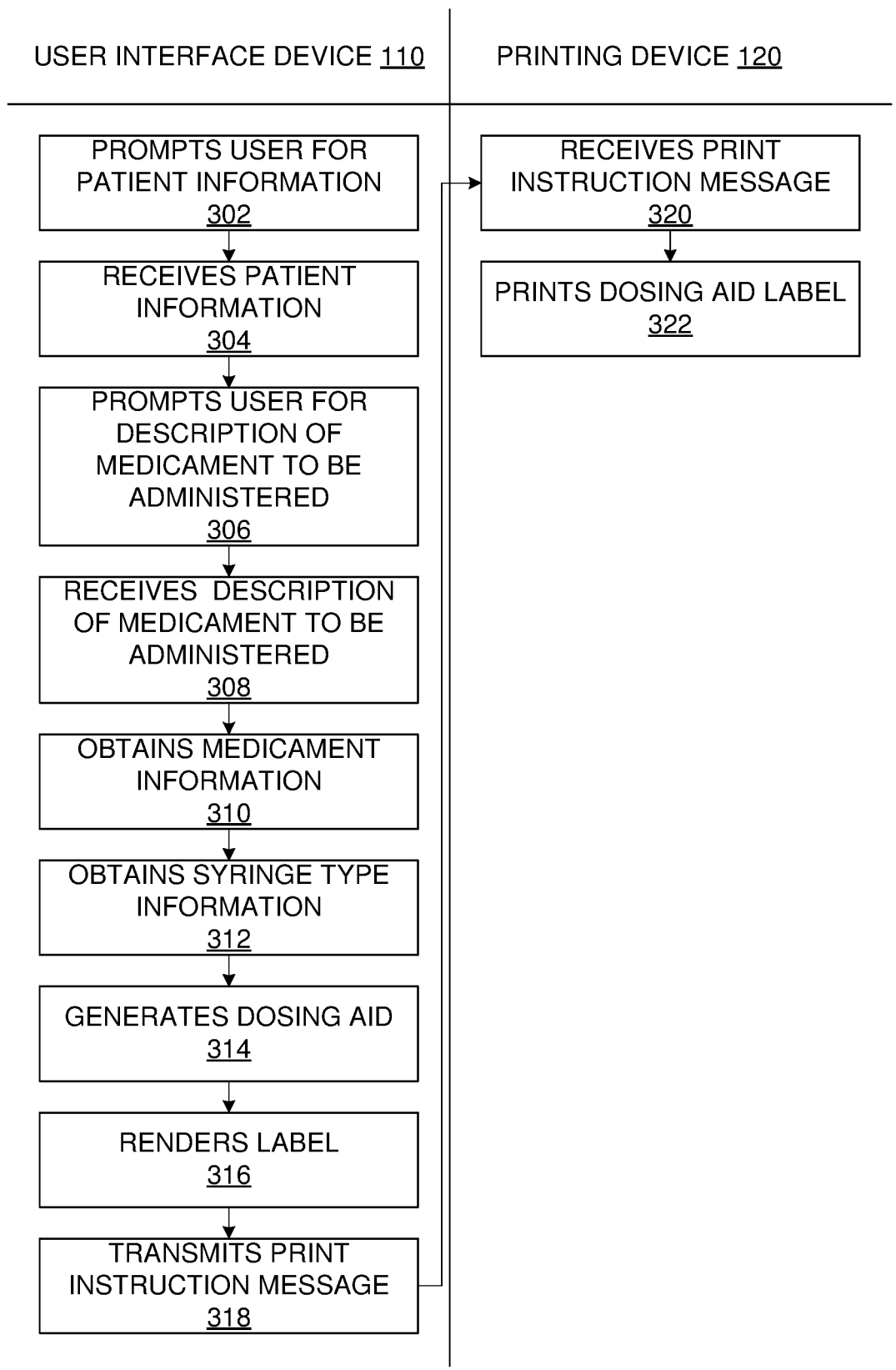
FIG. 3 is a swim-lane flow diagram which illustrates a method for generating a dosing aid label.
Figure 4:
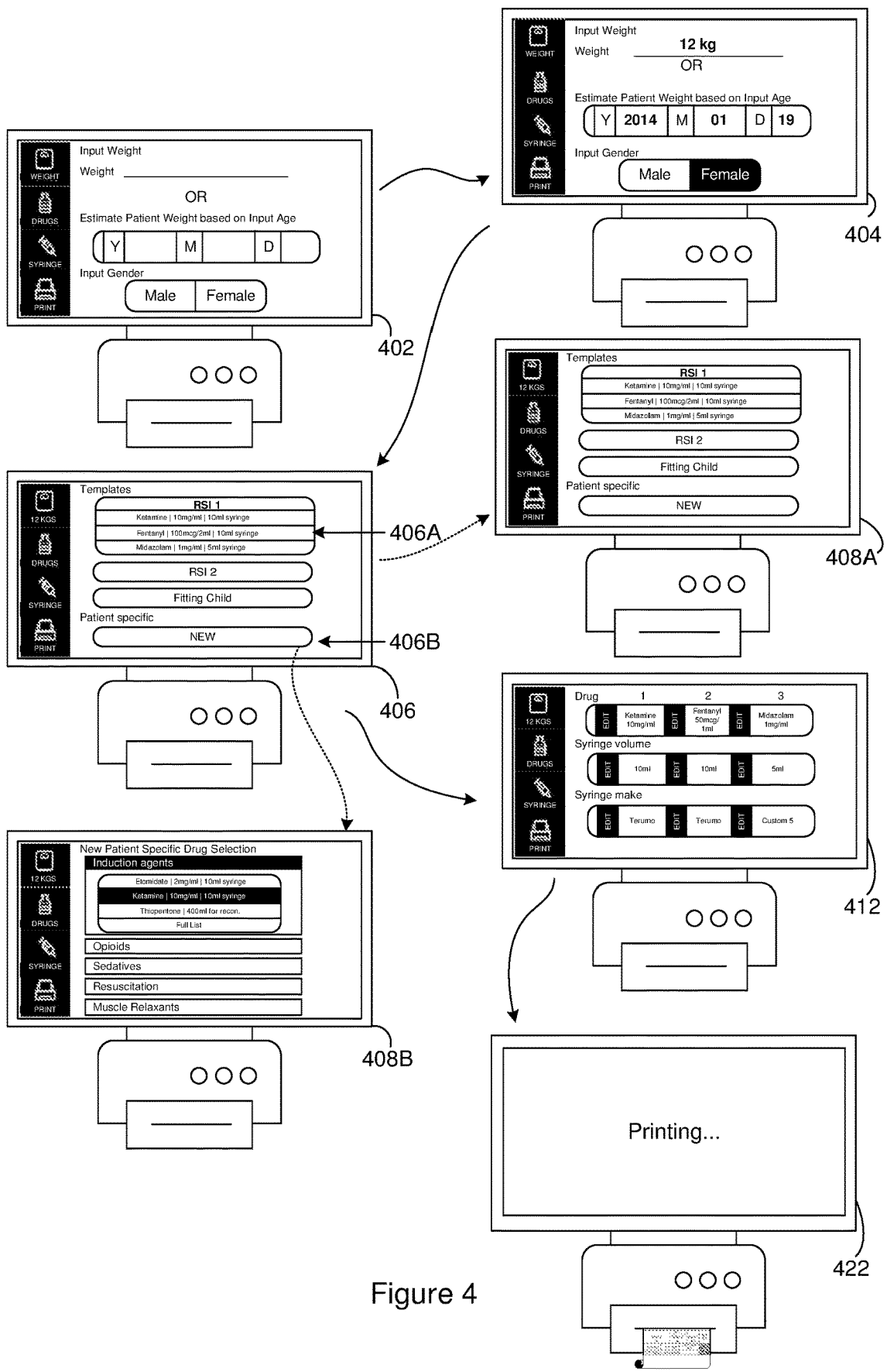
FIG. 4 is a schematic flow diagram which illustrates an exemplary graphical user interface which may be provided by a user interface device described herein.

FIG. 3 is a swim-lane flow diagram which illustrates a method for generating a dosing aid label for a syringe which may be implemented by a system, such as the system (100) as described above. The method is described with reference to FIG. 3 as well as FIG. 4, which illustrates an exemplary graphical user interface which may be provided by the user interface device (110).

A user, such as a healthcare professional at a health facility, may need to administer a patient with a dose of a medicament. The patient may, for example, be suffering from a condition and may require a particular dose of a particular medicament. The dose required may be based on patient information relating to the patient, such as the patient's body weight, condition, gender, etc. The user may use the user interface device (110) to obtain the dosing information. The user may commence by, for example, launching a software application on the user interface device (110).

The user interface device (110) may prompt (302, 402) the user for patient information relating to the patient to whom the medicament is to be administered. In this exemplary embodiment, the user interface device prompts the user for a patient weight or alternatively for a patient age and a patient gender for determining an estimated patient weight. The user uses an input device of the user interface device to input the patient information.

The user interface device (110) receives (304, 404) the patient information, in this embodiment either in the form of patient weight or patient age and gender. In other implementations the patient information may be received from a tag associated with the patient (e.g. via a barcode scanner, radio frequency antenna or camera). The user interface device (110) may prompt (306, 406) the user for medicament information relating to a medicament to be administered to the patient.

Prompting (306, 406) the user for medicament information (such as a description of a medicament to be administered) may include providing the user with a menu from which the user can select preconfigured regimens (406A) or specific medicaments (406B), which may be arranged alphabetically, in classifications or in any other appropriate manner. In some cases, the user may be able to search for medicaments. The user uses an input device of the user interface device (110) to input a description of the medicament to be administered. The user may be able to input a number of descriptions of medicaments to be administered. Once input, the user interface device (110) may display each description (e.g. the name of the medicament) while allowing the user to continue inputting descriptions of further medicaments. In other embodiments, the user interface device (110) may include or have access to a barcode scanner, camera or radio frequency antenna to enable the user to input medicament information by displaying a tag in the form of a label, barcode or radio frequency tag associated with the medicament packaging.

The user interface device (110) receives (308, 408) medicament information, in this exemplary case including a description of a medicament to be administered. The description may either be a description of a regimen to be administered (408A) or descriptions one or more specific medicaments to be administered (408B). In implementations where the user interface device (110) receives the medicament description only, the user interface device (110) may use the received medicament description to obtain (310) further medicament information which may include one or more of a recommended dosage of the medicament (e.g. X mg/kg) and concentration information, such as the concentration in which the medicament is available (e.g. in Y mg/ml ampoules). In some embodiments, the medicament information is included in and received from a tag (such as a medicament label) associated with the medicament and from which the description of the medicament to be administered was received. In other embodiments, the medicament information is obtained from a medicament information database.

The user interface device (110) obtains (312, 412) syringe type information relating to a type of syringe to be used to administer the medicament. The syringe type information at least includes the type of syringe to be used (e.g. make, model, capacity, etc.) and may also include marker information relating to one or more markers provided on a syringe of the type to be used. Obtaining (312) syringe type information may include determining an optimal type of syringe to be used based on one or more of the patient information, medicament information, stock levels, syringe costs and the like. For example, a syringe of suitable capacity and/or caliber may be determined and suggested. The user may also be able to select of a type of syringe to be used.

If a conventional syringe is selected, the marker information may be a syringe volume indication scale which corresponds to graduations provided on a syringe of the type to be used which indicates volumes within the syringe. Alternatively, the marker information may inform the size of label to be used or may include information relating to locations of one or more label markers provided on the syringe of the type to be used for facilitating placement of the label. In some cases, for example where labels are of a standardised size and the dosing scale is provided on the syringe in a standardised location, marker information may not be required.

The user interface device (110) generates (314) a dosing aid, in this scenario being a dosing scale associated with the patient information, medicament information and optionally syringe type information. The dosing scale may be generated dynamically in near real-time (e.g. a matter of seconds or less) based on the syringe type information, patient information and/or medicament information. Generating (314) the dosing scale may include calculating the dosing scale based on one or more of: the patient information, the medicament information, the syringe type information, dimensions of the label, information relating to the predetermined position and information relating to the sheet of material.

For example in the case of a simple weight-based dose, calculating the dosing scale may include converting a recommended weight-based dose of the medicament (e.g. in mg/kg) into a required dose of the medicament (e.g. in mg) for the patient's weight (in kg). Having determined the required dose (in mg), a volume calculation may be performed in order to determine the amount (e.g. in ml) of medicament which must be drawn from a certain ampoule for a given concentration of the medicament (e.g. in mg/ml). Then the positioning of the indication on the label (e.g. in x,y coordinates) must be determined, taking into account the size of the label and marker information relating to markers provided on the syringe. The positioning of the indication is required to be such that when the label is affixed to the syringe in the predetermined position, the indication correctly translates the volume defined by the stopper aligned therewith into the amount of medicament (in ml) which must be drawn into or administered from the syringe.

In other embodiments, generating (314) the dosing scale may include accessing a database in which a number of pre-generated dosing scales are stored, each of the pre-generated dosing scales being associated with the syringe type information, patient information and/or medicament information.

The dosing scale includes one or several indications arranged to translate a volume defined by a position of a stopper within a syringe of the type to be used into dosing information relating to a dose of the medicament to be administered to the patient. The dosing scale is calibrated based on the scale operatively being located in a predetermined position on the syringe.

In some embodiments, the user interface device (110) may render (316) a dosing aid label and display the label to the user. Rendering the label may include determining or accessing the dimensions of the label and locating the dosing aid, in this case being the dosing scale, on the label in a particular position such that the label cooperates with markers provided on the syringe to locate the dosing scale on the syringe in the predetermined position. Rendering the label may also include providing additional information on the label. The additional information may include patient information, medicament information and syringe type information. In some embodiments, positioning information may be provided on the label. The positioning information may be arranged to facilitate positioning the dosing scale in the predetermined position relative to one or more markers on the syringe. The positioning information may, for example, be in the form of a syringe volume indication scale which operatively should be aligned with graduations provided on the syringe in order to locate the dosing scale in the predetermined position. The dosing aid label may be rendered in any appropriate format, such as a PDF or the like.

The user may input an instruction to print a dosing aid label including the dosing aid, in this case being a dosing scale. The user interface device (110) receives the instruction and transmits (318) a print instruction message to the printing device (120). The instruction message instructs the printing device to print the label. The instruction message may include the rendered label. Alternatively, the printing device may render a label responsive to receiving the instruction message.

The printing device (120) receives (320) the printing instruction message from the user interface device (110) and prints (322, 422) the dosing aid label. The label is printed on a generally rectangular sheet of flexible material and has the dosing scale and optionally additional information provided thereon. The label may have an adhesive provided on an operatively back surface thereof for affixing the label to the syringe. The label may be transparent, semi-transparent or may be provided with a transparent window to facilitate alignment of the stopper of the syringe with the indications of the dosing scale. Once the label has been printed on the sheet of material, it may be affixed to the syringe and may thereafter be used to guide preparation and/or administration of the dose of the medicament to the patient. In other embodiments, the label may be printed directly on the syringe.

Figure 5A:
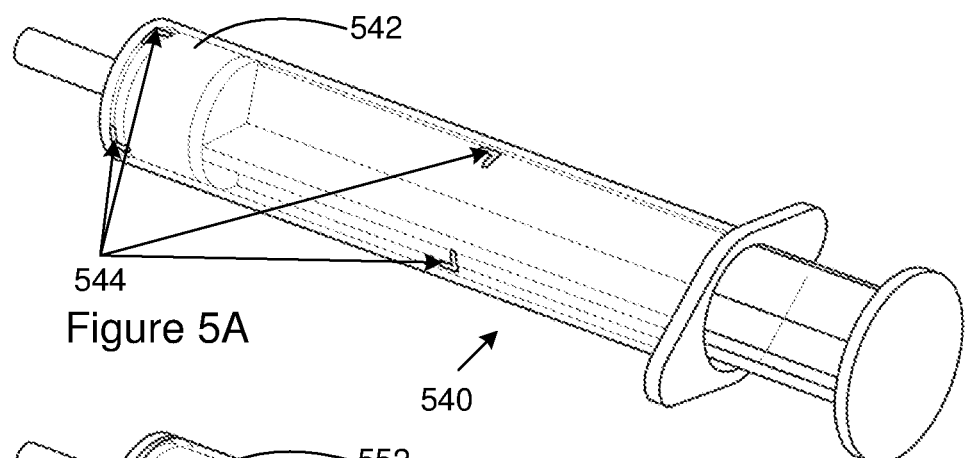
FIG. 5A is a three-dimensional view of a first exemplary syringe described herein.
Figure 5B:
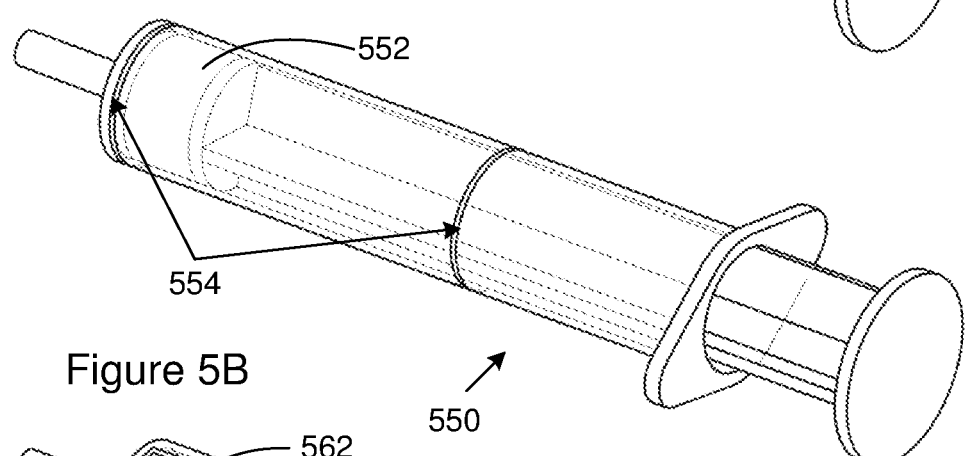
FIG. 5B is a three-dimensional view of a second exemplary syringe described herein.
Figure 5C:
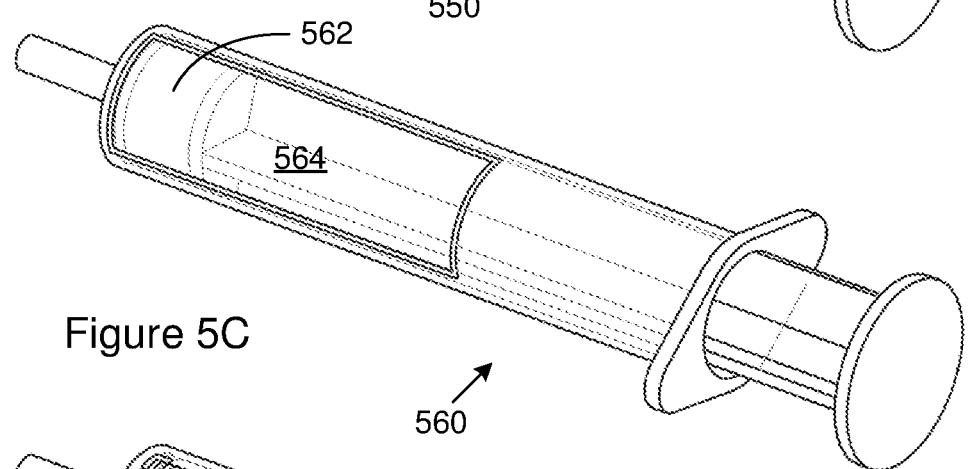
FIG. 5C is a three-dimensional view of a third exemplary syringe described herein.
Figure 5D:
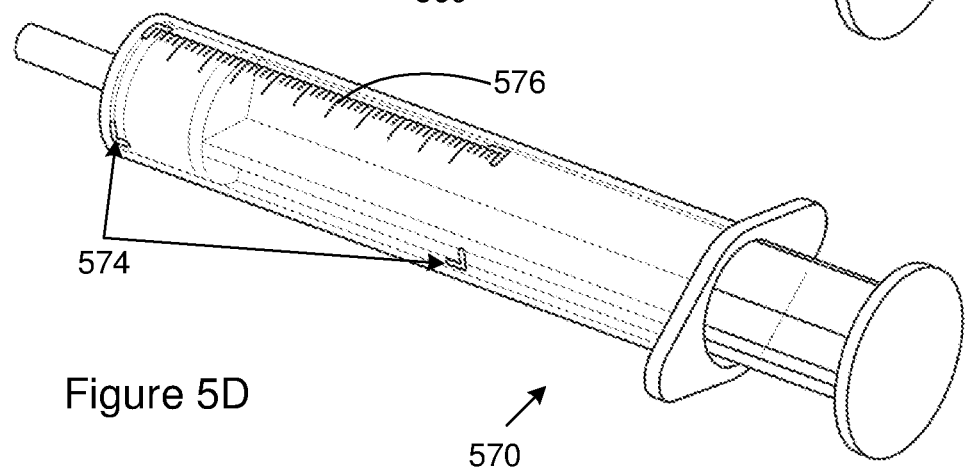
FIG. 5D is a three-dimensional view of a fourth exemplary syringe described herein.
Figure 6:
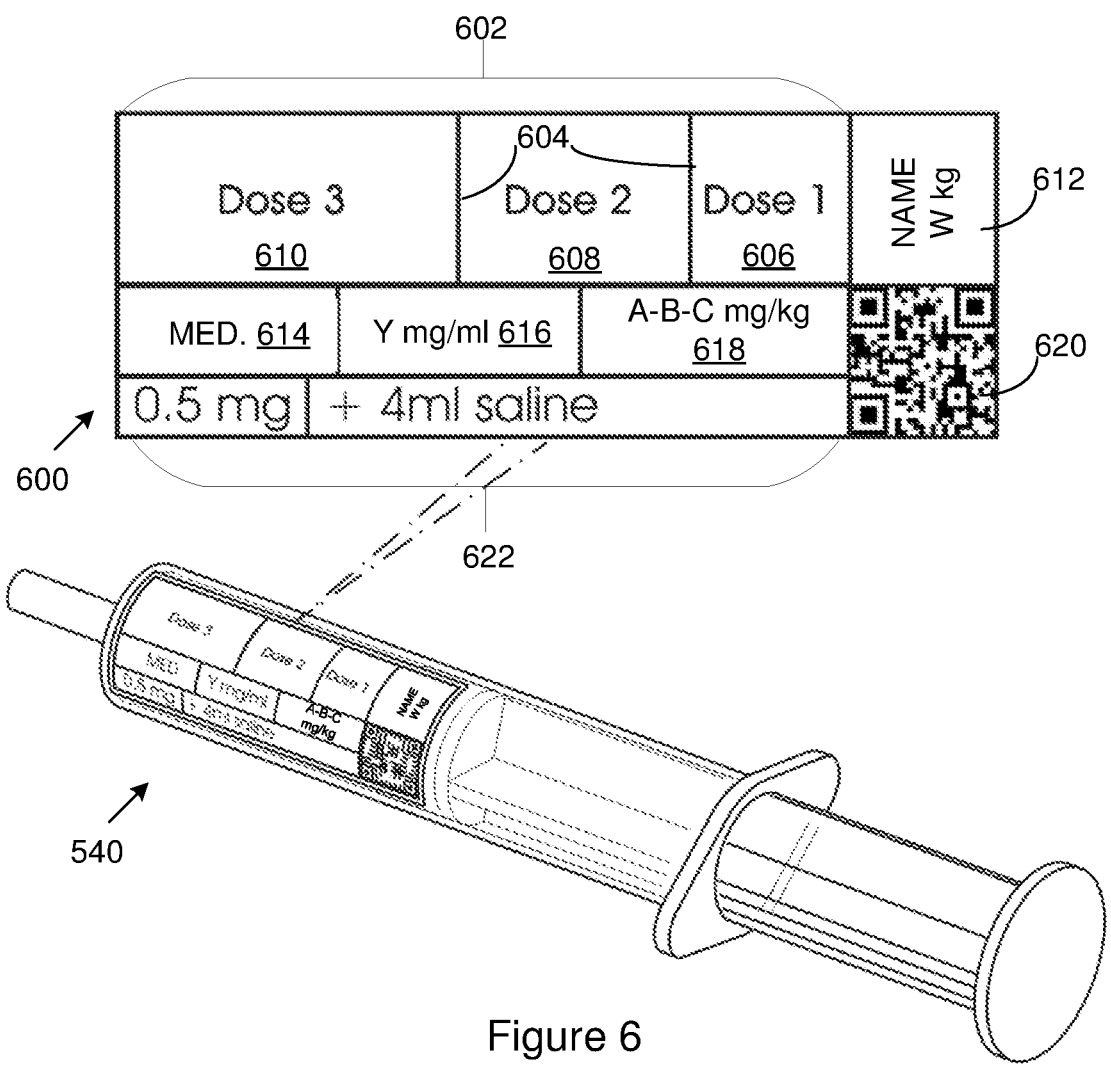
FIG. 6 is a schematic diagram which illustrates an exemplary dosing aid label affixed to a syringe.
Figure 7:
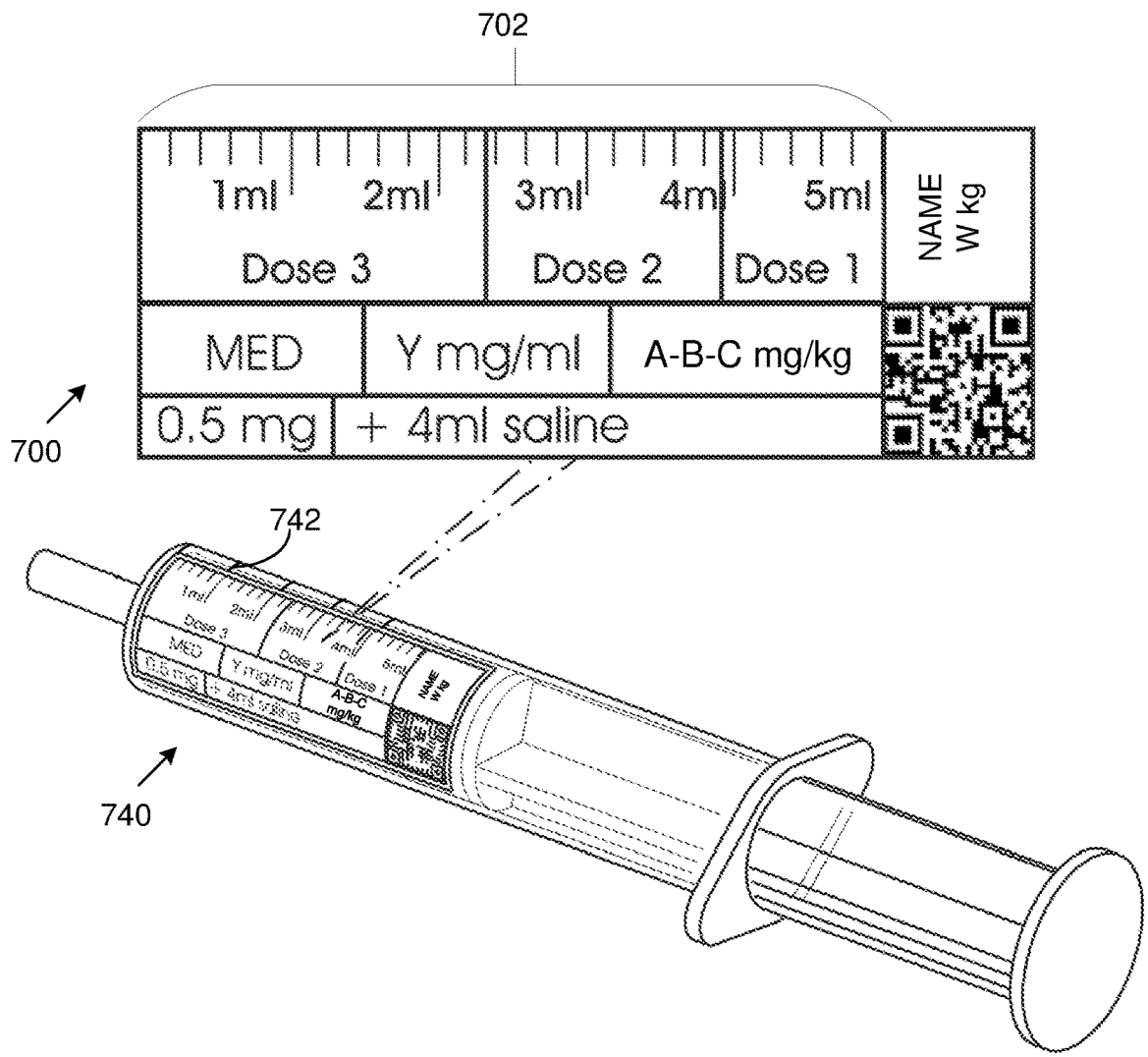
FIG. 7 is a schematic diagram which illustrates an exemplary dosing aid label affixed to a syringe according to another embodiment.

FIGS. 5A to 5D illustrate exemplary custom syringes according to various embodiments described herein and FIGS. 6 and 7 illustrate syringes having labels as described herein affixed thereto. The custom syringes may be provided with or without graduations indicating volumes within the syringe. In some cases, a syringe volume indication scale may be provided on the labels to indicate volumes within the syringes.

The syringe (540) illustrated in FIG. 5A is similar to a conventional syringe and has barrel and a stopper (542) movable within the barrel to draw and administer medicaments. The syringe (540) has label markers (544) provided thereon to facilitate locating a dosing scale provided on a label in a predetermined position on the syringe (540). The label markers (544) may be arranged to cooperate with the dosing aid label in order to facilitate positioning of the dosing scale on the syringe in the predetermined position. The specific positioning of the label markers (544) on the syringe (540) may be selected to facilitate location of the dosing aid label on the syringe such that the syringe locates in the predetermined position. The label markers (544) in this embodiment are corner guides printed or formed on the syringe and arranged to align with corners of a label to be affixed to the syringe such that the label (in the correct orientation relative to the syringe) may be correctly calibrated and that a dosing scale provided thereon is in a predetermined position.

The syringe (550) illustrated in FIG. 5B has label markers (554) in the form of two parallel, spaced apart lines printed or formed on a surface of a barrel of the syringe (550) and which extend (at least partially) circumferentially around the barrel. The lines are spaced apart so as to align with parallel minor edges of a label, such that affixing the label to the barrel of the syringe in-between the two lines positions the dosing scale provided on the label in a predetermined position.

The syringe (560) illustrated in FIG. 5C has label markers (564) in the form of a formation formed on the syringe. The formation (564) in this embodiment is a depression or recess which extends partially along a length of a barrel of the syringe and at least partially around the barrel. The depression defines a zone having a shape and size corresponding to that of a cooperating label such that locating the label within the zone positions a dosing scale provided on the label in a predetermined position.

The syringe (570) illustrated in FIG. 5D is similar to that of FIG. 5A, except in that in addition to label markers (574) in the form of corner guides being provided, the syringe (570) also includes graduations (576) which indicate volumes within the syringe (570).

In the exemplary scenario illustrated in FIG. 6, the dosing aid label (600) is for use with and is affixed to a particular syringe (e.g. 540) as described herein (e.g. a syringe provided specifically for use with the system and method described herein). The label (600) has a dosing scale (602) provided thereon. The dosing scale (602) includes a number of indications (604) which are arranged to translate a volume defined by a position of a stopper (542) within the syringe (540) into dosing information relating to a dose of the medicament to be administered to the patient. In this exemplary scenario, the dosing information is in the form of a first dose (606), a second dose (608) and a third dose (610). The label (600) also has patient information (612) in the form of the patient's name and the patient's body weight. The label (600) also includes the name of the medicament (614), the concentration of the medicament (616) and the recommended dosage of the medicament (618). The label (600) further includes a graphical code (620) in the form of a two-dimensional barcode, in which patient information and/or medicament information may be encoded (e.g. for use with anaesthetic systems drug administration tracking software), as well a dilution assistance scale (622) for providing a visual guide to assist with dilution of the medicament.

The label (600) is printed on an operatively front surface of a flexible sheet of material. The flexible sheet of material may include an adhesive on an operatively back surface thereof for adhering the label (600) to the syringe (540). In this exemplary scenario, the sheet of material is of standardised dimensions which are selected to cooperate with label markers (544) provided on the syringe (540) and to thereby facilitate locating the dosing scale (602) in the predetermined position on the syringe (540). The predetermined position is a position in which indications of the dosing scale are positioned correctly along a length of the barrel of the syringe.

Turning now to FIG. 7 an exemplary dosing aid label (700) is shown affixed to a conventional syringe (740). The conventional syringe (740) has graduations (742) which indicate volumes within the syringe and the label (700) is provided with positioning information in the form of a syringe volume indication scale (702) which is arranged to facilitate positioning of the dosing scale in the predetermined position. By aligning indications of the syringe volume indication scale (702) included on the label (700), with the graduations (742) provided on the syringe, the label may be affixed to the syringe with the dosing scale in the predetermined position.

Figure 8B:
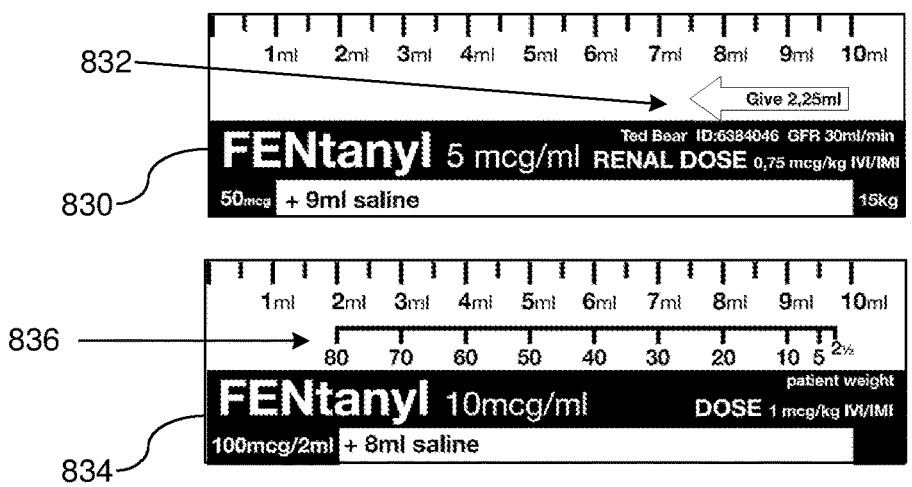
FIG. 8B illustrates a second set of exemplary dosing aid labels which may be provided by the system and method described herein.
Figure 8A:
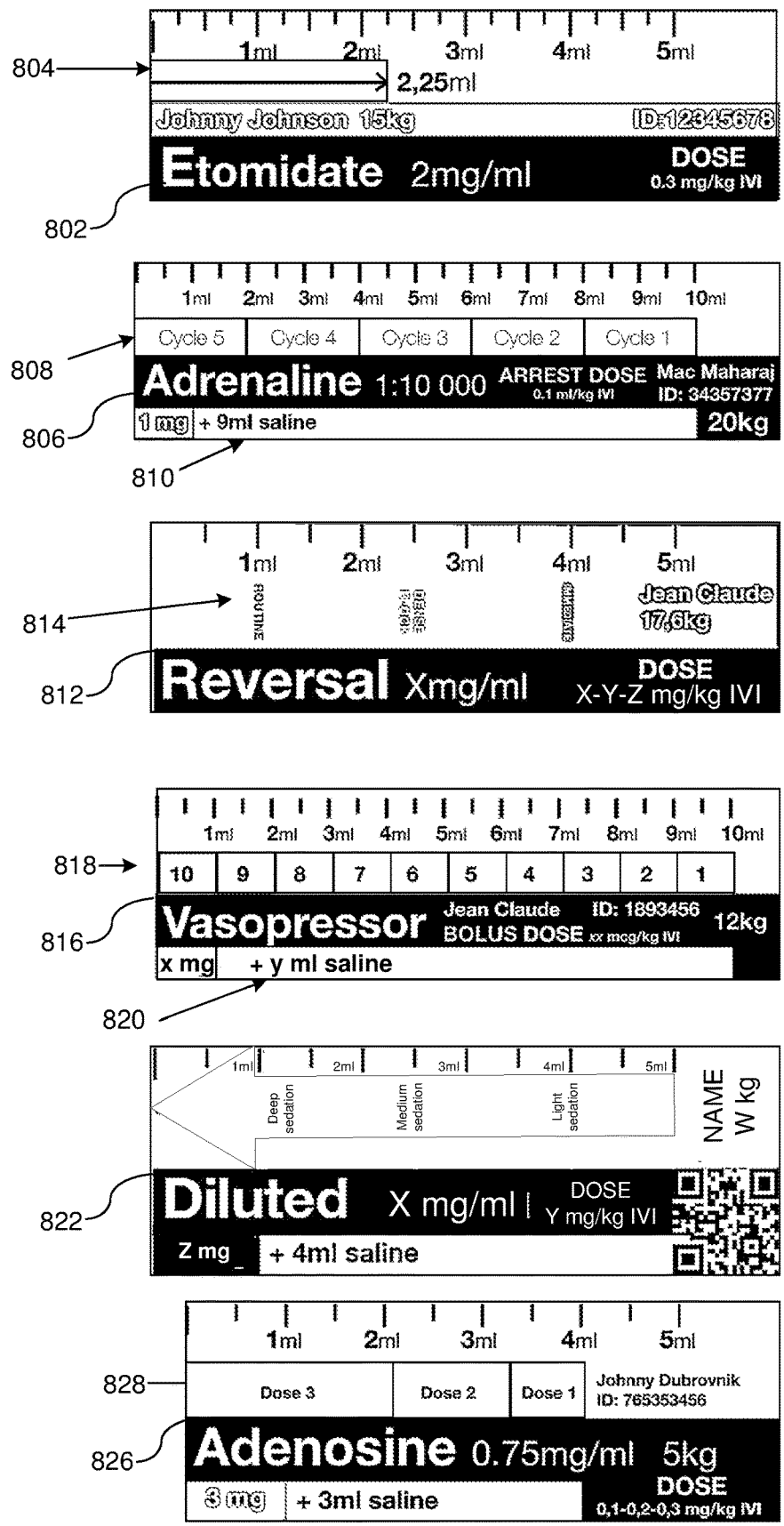
FIG. 8A illustrates a first set of exemplary dosing aid labels which may be provided by the system and method described herein.

Some exemplary labels which may be provided by the system and method described herein are illustrated in FIGS. 8A and 8B. The labels may be colour-coded according to international colour coding systems used for labels to indicate the type of medicament to be held in the syringe. The labels may be printed on flexible sheets of material configured to be affixed to a syringe or may be printed directly on the syringe. In some cases, the labels may be sized so as to correspond with markers provided on corresponding syringes so as to facilitate placement of the label on the syringe with the dosing scale in the predetermined position.

A first exemplary dosing aid label (802) includes a patient-specific dosing scale (804) which includes one indication. The indication indicates the extent to which a stopper of the syringe must be drawn out when drawing the medicament (in this case being Etomidate) so as to draw the required dose of the medicament for the particular patient. The required dose in this case is specific to the patient's weight. The dosing scale (804) accordingly permits the preparation of a dose of the medicament with significantly reduced cognitive burden on the part of the user preparing the dose.

A second exemplary dosing aid label (806) is for the administration of Adrenaline. The label includes a dosing scale (808) which indicates doses of the Adrenaline which should be administered for each cycle during cardiopulmonary resuscitation (CPR). The dosing scale (808) translates volumes within the syringe into five doses of adrenaline for each cycle of CPR. The dosing scale is specific to the patient's weight, in this example being 20 kg. The label (806) also shows the final concentration of the Adrenaline-saline mixture (1:10,000) as well as the dose which is administered (being 0.1 ml/kg). The label also includes a dilution assistance scale (810) to guide a user in preparing the mixture. The dilution assistance scale (810) indicates the volume of medicament and the volume of diluent required to be drawn into the syringe in order to achieve the recommended final concentration of the mixture. The label further includes positioning information in the form of a volume indication scale which is arranged to align with graduations provided on a syringe which is to be used to administer the Adrenaline and patient information in the form of a patient name, identifier and body weight.

Figure 8C:
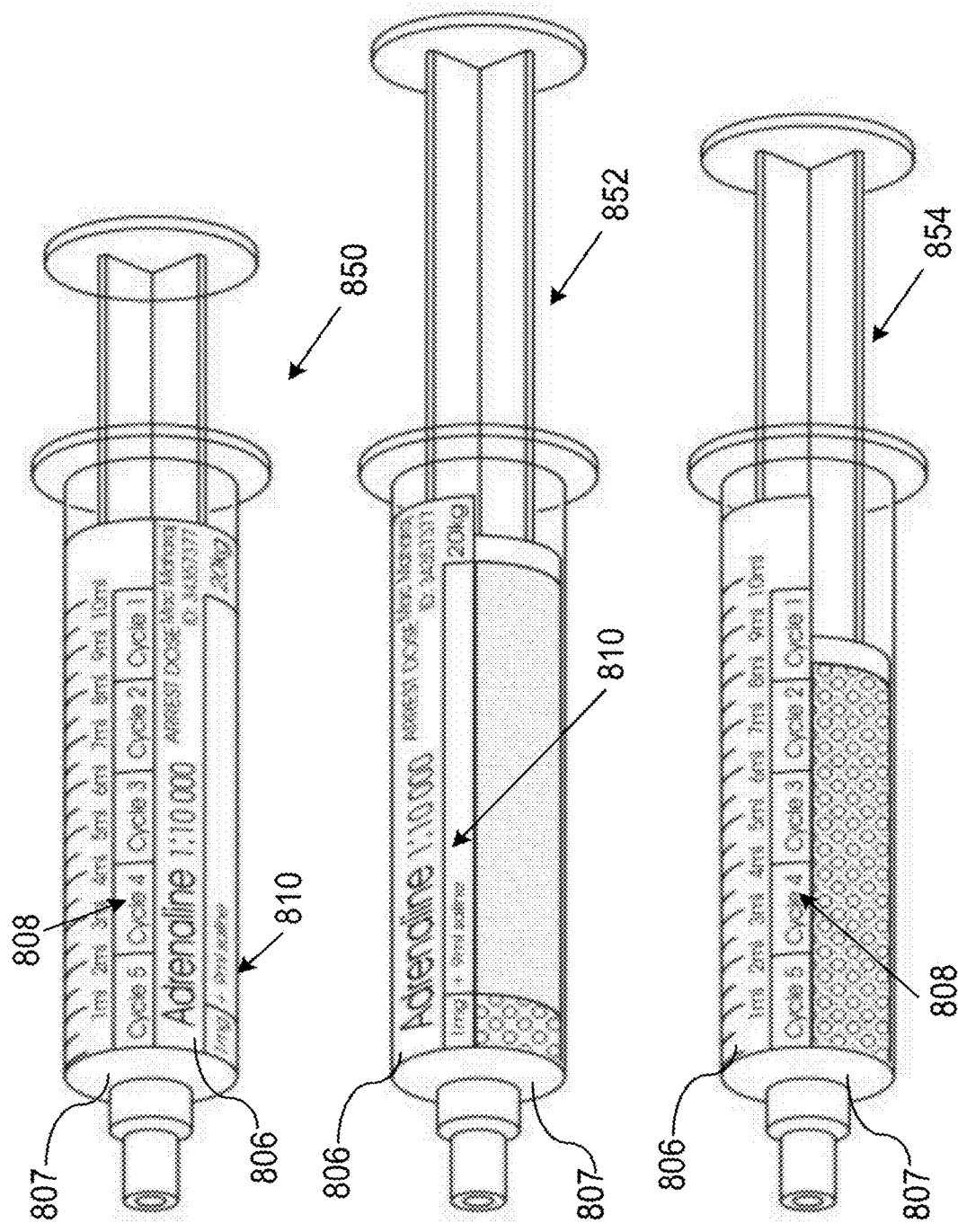
FIG. 8C illustrates exemplary use of a dosing aid label described herein.

With reference to FIG. 8C, once the label (806) has been affixed (850) to a syringe (807) the dilution assistance scale (810) may be used in a first stage (852) to guide preparation of the medicament. In the example illustration, the dilution assistance scale may be used guide appropriate dilution of the medicament by first drawing 1 mg of the medicament and then 9 ml of saline so as to arrive at the correct final concentration of the Adrenaline-saline mixture (0.1 mg/ml or 1:10,000 as commonly described). Once the medicament has been prepared, in a next stage (854) the medicament may be administered in cycles according to the dosing scale (808). The amount of medicament administered in each cycle being specific to the patient's weight.

Returning to FIG. 8A, a third exemplary dosing aid label (812) includes a dosing scale (814) in the form of a titrated to effect scale. The dosing scale (814) guides a healthcare professional in administering an agent with multiple different doses for different conditions, i.e. doses that are titrated to effect. In the example illustrated the clinical scenario is a label for an agent to reverse neuromuscular blockade which includes a dosing scale (814) having indications corresponding to "immediate", "dense block" and "routine" doses of the medicament. These indications are based on patient information, such as the patient weight and/or the patient condition. The label further includes positioning information in the form of a volume indication scale which is arranged to align with graduations provided on a syringe which is to be used to administer the medicament as well as patient information.

A fourth exemplary dosing aid label (816) includes a dosing scale (818) in the form of a bolus dose scale. When administering bolus doses it can be convenient, from the perspective of the user administering the bolus dose, to do so one milliliter at a time (e.g. to plunge the plunger from 10 ml to 9 ml for the first bolus dose and from 9 ml to 8 ml for the second bolus dose). Of course, depending on the concentration of the medicament, and the weight of the patient, this may not always be possible. The system and method described herein enable the inclusion of an adapted dilution scale (820) which is calibrated to guide dilution of a medicament such that a one milliliter bolus dose will administer the correct dose (in mg) of the medicament. In other words, the concentration of the diluted mixture is such that administering one milliliter of the mixture effectively administers the correct dose of the medicament in milligrams. The bolus dose scale (818) is calibrated to work together with the adapted dilution scale (820) so as to guide a user in diluting a medicament to an appropriate concentration, so as to be able to administer useful bolus doses of a medicament (i.e. doses of reasonable volumes) even in the case of a small pediatric patient. In this example, a vasopressor label for administering bolus doses is provided. The bolus dose scale (818) provides indications which translate certain volumes defined within a syringe to be used into ten doses of the medicament, where each bolus dose corresponds to a syringe volume of 1 milliliter.

A fifth exemplary dosing aid label (822) is a label for a diluted medicament. This label provides a dosing scale which guides administration of a medicament titrated to effect for a full syringe. In other words, the scale guides the extent to which the stopper must be plunged in order to administer the correct dose in order to achieve a desired result. Indications on the dosing scale provide condition-based dosing information, i.e. in this example whether a sedative to be administered to a patient is required to achieve "light sedation", "medium sedation" or "deep sedation".

A sixth exemplary dosing aid label (826) includes a dosing scale in the form of a multi-dose adjustment scale (828) which indicates first, second and third doses. The multi-dose adjustment scale (828) guides a user in administering doses of a medicament in which multiple successive, varying doses are administered over time. In this example, the medicament requires three doses, with each subsequent dose increasing in quantity. An example of such a medicament which requires successive, increasing doses is Adenosine.

FIG. 8B shows two exemplary dosing aid labels (830, 834) which guide the preparation and/or administration of Fentanyl. The first dosing aid label (830) is a patient specific label and includes a dosing scale (832) having one indication which guides a user in administering an appropriate dose of Fentanyl for the particular patient. In this exemplary scenario, the patient has a body weight of 15 kg and a glomerular filtration rate (GFR) of 30 ml/min. GFR gives an indication of the degree of renal failure. By utilising the system and method described herein, this patient information can be used to generate the appropriate dosing scale and dilution assistance scale so that the appropriate dose of Fentanyl can be prepared and administered to this particular patient (taking into account the patient's condition). The second label (834) shown in FIG. 8B is a patient agnostic label which includes a dosing scale (836) in the form of a patient weight scale. The dosing scale may be an example of a pre-generated dosing scale which may be stored in a database in association with one or more of patient information, medicament information and syringe type information and which, using the system and method described, herein may be accessed and included in the label which is printed. As the label is not specific to a particular patient, the user administering the dose would have to take into account the patient condition (e.g. degree of renal failure and weight) in administering the dose.

The described system and method accordingly enable the generation of a dosing aid label for a syringe. The dosing aid label provides a dosing aid to a user to guide preparation and/or administration of a dose or doses of a medicament. The dosing aid may be specific to a patient and medicament and is provided by way of a dosing scale or instructions included on a label. The label may be printed on a sheet of material configured for attachment to a syringe or directly on the syringe. The label may be generated and printed in near real time to avoid vast quantities of stock of many different types of labels having to be maintained and also to enable patient-specific labels, which take into account patient condition, to be generated and printed. The described system and method may also enable in situ generation of dosing aid labels such as for example in the ward, emergency room, etc.

In using the system and method described herein, in one exemplary scenario, a healthcare professional may input the weight of a patient, input the description of the medicament the professional wishes to administer to the patient and select a type of syringe that will be used to administer the medicament. The system then outputs a bespoke label, either of a sheet of material configured for attachment to a syringe or onto the syringe directly, which includes a dosing aid which guides the healthcare professional in preparing and administering the required dose of the medicament. The dosing aid may be a dosing scale or instructions which guide administration of the dose of the medicament.

Figure 9:
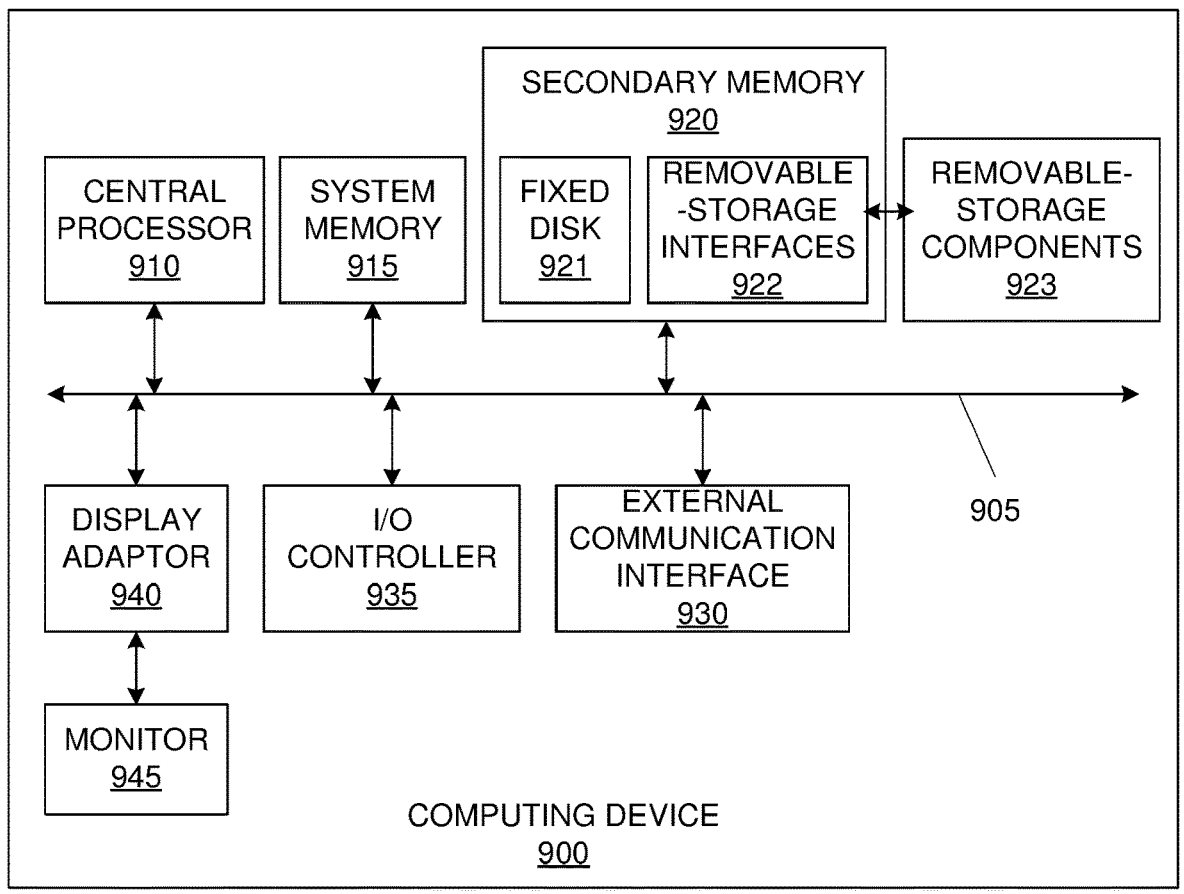
FIG. 9 illustrates an example of a computing device in which various aspects of the disclosure may be implemented; and, FIG. 10 shows a block diagram of a communication device that may be used in embodiments of the disclosure.

FIG. 9 illustrates an example of a computing device (900) in which various aspects of the disclosure, for example the user interface device, may be implemented. The computing device (900) may be suitable for storing and executing computer program code. The various participants and elements in the previously described system diagrams may use any suitable number of subsystems or components of the computing device (900) to facilitate the functions described herein. The computing device (900) may include subsystems or components interconnected via a communication infrastructure (905) (for example, a communications bus, a cross-over bar device, or a network). The computing device (900) may include at least one central processor (910) and at least one memory component in the form of computer-readable media.

The memory components may include system memory (915), which may include read only memory (ROM) and random access memory (RAM). A basic input/output system (BIOS) may be stored in ROM. System software may be stored in the system memory (915) including operating system software.

The memory components may also include secondary memory (920). The secondary memory (920) may include a fixed disk (921), such as a hard disk drive, and, optionally, one or more removable-storage interfaces (922) for removable-storage components (923). The removable-storage interfaces (922) may be in the form of removable-storage drives (for example, magnetic tape drives, optical disk drives, etc.) for corresponding removable storage-components (for example, a magnetic tape, an optical disk, etc.), which may be written to and read by the removable-storage drive. The removable-storage interfaces (922) may also be in the form of ports or sockets for interfacing with other forms of removable-storage components (923) such as a flash memory drive, external hard drive, or removable memory chip, etc.

The computing device (900) may include an external communications interface (930) for operation of the computing device (900) in a networked environment enabling transfer of data between multiple computing devices (900). Data transferred via the external communications interface (930) may be in the form of signals, which may be electronic, electromagnetic, optical, radio, or other types of signal. The external communications interface (930) may enable communication of data between the computing device (900) and other computing devices including servers and external storage facilities. Web services may be accessible by the computing device (900) via the communications interface (930). The external communications interface (930) may also enable other forms of communication to and from the computing device (900) including, voice communication, near field communication, Bluetooth™, etc.

The computer-readable media in the form of the various memory components may provide storage of computer-executable instructions, data structures, program modules, and other data. A computer program product may be provided by a computer-readable medium having stored computer-readable program code executable by the central processor (910). A computer program product may be provided by a non-transient computer-readable medium, or may be provided via a signal or other transient means via the communications interface (930).

Interconnection via the communication infrastructure (905) allows a central processor (910) to communicate with each subsystem or component and to control the execution of instructions from the memory components, as well as the exchange of information between subsystems or components.

Peripherals (such as printers, scanners, cameras, or the like) and input/output (I/O) devices (such as a mouse, touchpad, keyboard, microphone, or the like) may couple to the computing device (900) either directly or via an I/O controller (935). These components may be connected to the computing device (900) by any number of means known in the art, such as a serial port. One or more monitors (945) may be coupled via a display or video adapter (940) to the computing device (900).

Figure 10:
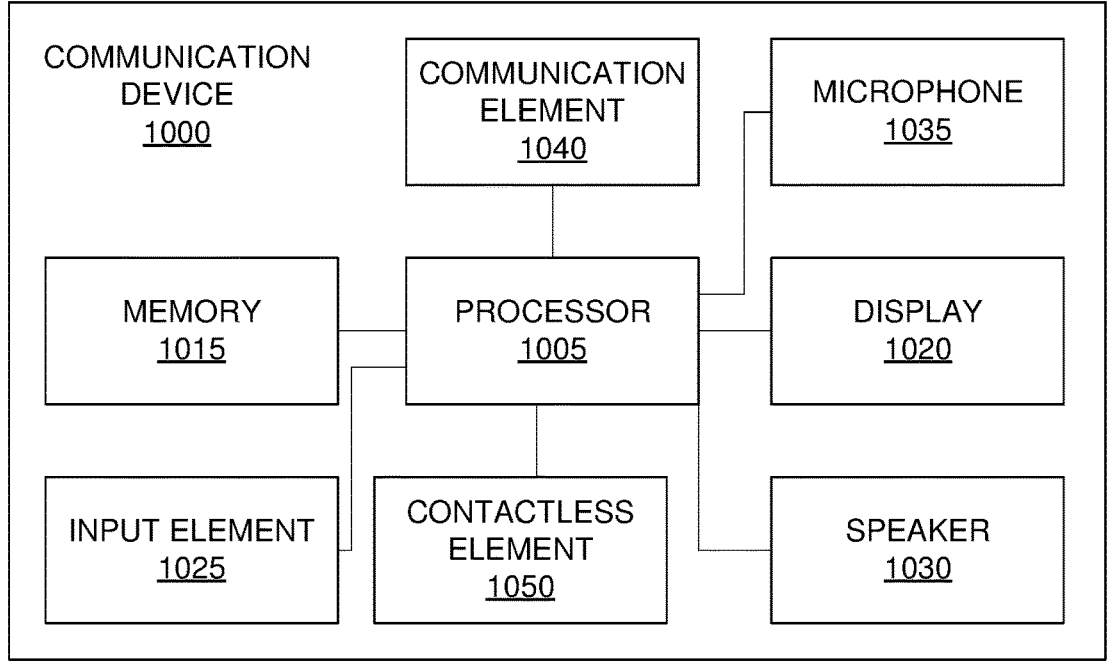

FIG. 10 shows a block diagram of a communication device (1000) that may be used in embodiments of the disclosure. The communication device (1000) may be a cell phone, a feature phone, a smart phone, a satellite phone, or a computing device having a phone capability.

The communication device (1000) may include a processor (1005) (e.g., a microprocessor) for processing the functions of the communication device (1000) and a display (1020) to allow a user to see the phone numbers and other information and messages. The communication device (1000) may further include an input element (1025) to allow a user to input information into the device (e.g., input buttons, touch screen, etc.), a speaker (1030) to allow the user to hear voice communication, music, etc., and a microphone (1035) to allow the user to transmit his or her voice through the communication device (1000). The processor (1010) of the communication device (1000) may connect to a memory (1015). The memory (1015) may be in the form of a computer-readable medium that stores data and, optionally, computer-executable instructions.

The communication device (1000) may also include a communication element (1040) for connection to communication channels (e.g., a cellular telephone network, data transmission network, Wi-Fi™ network, satellite-phone network, Internet network, Satellite Internet Network, etc.). The communication element (1040) may include an associated wireless transfer element, such as an antenna. The communication element (1040) may include a subscriber identity module (SIM) in the form of an integrated circuit that stores an international mobile subscriber identity and the related key used to identify and authenticate a subscriber using the communication device (1000). One or more subscriber identity modules may be removable from the communication device (1000) or embedded in the communication device (1000).

The communication device (1000) may further include a contactless element (1050), which is typically implemented in the form of a semiconductor chip (or other data storage element) with an associated wireless transfer element, such as an antenna. The contactless element (1050) may be associated with (e.g., embedded within) the communication device (1000) and data or control instructions transmitted via a cellular network may be applied to the contactless element (1050) by means of a contactless element interface (not shown). The contactless element interface may function to permit the exchange of data and/or control instructions between mobile device circuitry (and hence the cellular network) and the contactless element (1050). The contactless element (1050) may be capable of transferring and receiving data using a near field communications (NFC) capability (or near field communications medium) typically in accordance with a standardised protocol or data transfer mechanism (e.g., ISO 14443/NFC). Near field communications capability is a short-range communications capability, such as radio-frequency identification (RFID), Bluetooth™, infra-red, or other data transfer capability that can be used to exchange data between the communication device (1000) and an interrogation device. Thus, the communication device (1000) may be capable of communicating and transferring data and/or control instructions via both a cellular network and near field communications capability.

The foregoing description of the embodiments of the invention has been presented for the purpose of illustration; it is not intended to be exhaustive or to limit the invention to the precise forms disclosed. Persons skilled in the relevant art can appreciate that many modifications and variations are possible in light of the above disclosure. Some portions of this description describe the embodiments of the invention in terms of algorithms and symbolic representations of operations on information. These algorithmic descriptions and representations are commonly used by those skilled in the data processing arts to convey the substance of their work effectively to others skilled in the art. These operations, while described functionally, computationally, or logically, are understood to be implemented by computer programs or equivalent electrical circuits, microcode, or the like. The described operations may be embodied in software, firmware, hardware, or any combinations thereof.

It should be appreciated that components or modules described herein may have the required configuration and/or arrangement of hardware, software, firmware or the like for performing their associated functions, steps, processes and/or operations. The software components or functions described in this application may be implemented as software code to be executed by one or more processors using any suitable computer language such as, for example, Java™, C++, or Perl™ using, for example, conventional or object-oriented techniques. The software code may be stored as a series of instructions, or commands on a non-transitory computer-readable medium, such as a random access memory (RAM), a read-only memory (ROM), a magnetic medium such as a hard-drive or an optical medium such as a CD-ROM. Any such computer-readable medium may also reside on or within a single computational apparatus, and may be present on or within different computational apparatuses within a system or network.

Flowchart illustrations and block diagrams of methods, systems, and computer program products according to embodiments are used herein. Any of the steps, operations, or processes described herein may be performed or implemented with one or more hardware or software modules, alone or in combination with other devices. In one embodiment, a software module is implemented with a computer program product comprising a non-transient computer-readable medium containing computer program code, which can be executed by a computer processor for performing any or all of the steps, operations, or processes described. In some alternative implementations, the functions identified by the blocks may take place in a different order to that shown in the flowchart illustrations.

Finally, the language used in the specification has been principally selected for readability and instructional purposes, and it may not have been selected to delineate or circumscribe the inventive subject matter. It is therefore intended that the scope of the invention be limited not by this detailed description, but rather by any claims that issue on an application based hereon. Accordingly, the disclosure of the embodiments of the invention is intended to be illustrative, but not limiting, of the scope of the invention, which is set forth in the following claims.

Throughout the specification and claims unless the contents requires otherwise the word 'comprise' or variations such as 'comprises' or 'comprising' will be understood to imply the inclusion of a stated integer or group of integers but not the exclusion of any other integer or group of integers.

The invention claimed is:

1. A computer-implemented method for generating a dosing aid label for a syringe, the method comprising:
    receiving patient information relating to a specific patient to whom a medicament is to be administered;
    receiving medicament information relating to a medicament to be administered to the specific patient, the medicament information including one or more of a description of the medicament, a recommended dosage of the medicament and concentration information relating to the medicament;
    generating a dosing aid including a dosing scale associated with the patient information and medicament information, the dosing scale including at least one indication being arranged to translate a volume defined by a position of a stopper within the syringe into dosing information relating to a dose of the medicament to be administered to the specific patient for guiding administration of the dose of the medicament to the specific patient; and,
    transmitting a print instruction message to a printing device, the instruction message being configured to instruct the printing device to print a dosing aid label including the dosing aid, the label being printed either on the syringe or on a sheet of material configured to be affixed to the syringe, such that the dosing aid label can be used to guide administration of the dose of the medicament to the specific patient.

2. The method as claimed in claim 1 wherein receiving medicament information relating to the medicament includes receiving the medicament information from one of an input device of the user interface device or a tag or barcode associated with the medicament.

3. The method as claimed in claim 1 wherein receiving medicament information includes receiving a selection of a preconfigured regimen, the preconfigured regimen including a description of one or more medicaments, each of the one or more medicaments being associated with a recommended dosage of the medicament and a concentration of the medicament.

4. The method as claimed in claim 1 wherein receiving medicament information relating to the medicament includes obtaining the recommended dosage of the medicament and concentration information relating to the medicament from a medicament information database.

5. The method as claimed in claim 1 wherein generating the dosing aid includes generating the dosing scale the dosing scale being calibrated based on the dosing scale operatively being located on the syringe in a predetermined position.

6. The method as claimed in claim 5 including obtaining syringe type information relating to a type of syringe to be used to administer the medicament, the syringe type information at least including the type of syringe to be used.

7. The method as claimed in claim 6, wherein the syringe type information includes marker information relating to one or more markers provided on the syringe of the type to be used.

8. The method as claimed in claim 7 wherein generating the dosing scale includes generating a dosing scale associated with the patient information, medicament information and the syringe type information, and wherein the dosing scale is calibrated based on the scale operatively being located in a predetermined position relative to the one or more markers provided on the syringe of the type to be used.

9. The method as claimed in claim 7 wherein the marker information includes a syringe volume indication scale corresponding to markers in the form of graduations provided on the syringe of the type to be used which indicate volumes within the syringe, wherein transmitting the print instruction message includes transmitting a print instruction message configured to instruct the printing device to include the syringe volume indication scale on the sheet of material on which the label is printed, wherein the syringe volume indication scale is included along a first major edge of the sheet of material and adjacent the dosing scale, and wherein the syringe volume indication scale being provided on the label for alignment with the graduations provided on the syringe of the type to be used for location of the dosing scale in the predetermined position on the syringe.

10. The method as claimed in claim 6 wherein obtaining syringe type information includes determining the type of syringe to be used based on one or both of the patient information and medicament information.

11. The method as claimed in claim 5 wherein generating the dosing scale includes calculating the dosing scale based on one or more of: the patient information, the medicament information, syringe type information, dimensions of the label, information relating to the predetermined position and information relating to the sheet of material.

12. The method as claimed in claim 1 wherein the dosing aid includes instructions for steps to be performed by a user in order to administer the dose of the medicament.

13. The method as claimed in claim 1, wherein the dosing scale is for a patient of a specific weight and for the administration of a specific medicament.

14. The method as claimed in claim 1, wherein the indication is a line which defines a particular volume when the dosing scale is placed on the syringe in a predetermined position and when the stopper of the syringe aligned with the indication, and wherein the particular volume is a volume required to administer a given quantity of the medicament having a particular concentration.

15. The method as claimed in claim 1, wherein the generated dosing scale includes one or more of the group of: a body weight scale, a dilution assistance scale, an adapted dilution scale, an infusion administration assistance table, a bolus dose scale, a physiological-variable adjusted scale, an ideal body weight conversion scale, a titrated to effect scale, and a multi-dose adjustment scale.

16. A dosing aid system for generating a dosing aid label for a syringe, the dosing aid system including a memory for storing computer-readable program code and a processor for executing the computer-readable program code, the system comprising:
 a patient information receiving component for receiving patient information relating to a specific patient to whom a medicament is to be administered;
 a medicament information receiving component for receiving medicament information relating to a medicament to be administered to the specific patient, the medicament information including one or more of a description of the medicament, a recommended dosage of the medicament, and concentration information relating to the medicament;
 a dosing aid generating component for generating a dosing aid including a dosing scale associated with the patient information and medicament information, the dosing scale including at least one indication being arranged to translate a volume defined by a position of a stopper within the syringe into dosing information relating to a dose of the medicament to be administered to the specific patient for guiding administration of a dose of the medicament to the specific patient; and,
 a transmitting component for transmitting a print instruction message to a printing device, the instruction message being configured to instruct the printing device to print a dosing aid label including the dosing aid, the label being printed either on the syringe or on a sheet of material configured to be affixed to the syringe, such that the dosing aid label can be used to guide administration of the dose of the medicament to the specific patient.

17. The system as claimed in claim 16 including a user interface device and the printing device, the printing device comprising: a receiving component for receiving the print instruction message; and, a printer for printing the label directly on the syringe or on a sheet of material configured to be affixed to the syringe.

18. The system as claimed in claim 16 including the syringe having one or more label markers provided thereon, the one or more label markers being arranged to cooperate with the dosing aid label including a dosing scale, the one or more label markers facilitating positioning of the dosing scale on the syringe in a predetermined position, such that operatively with the label affixed to the syringe with the dosing scale in the predetermined position, the dosing scale translates volumes within the syringe into dosing information thereby to guide administration of a dose of a medicament to the specific patient.

\* \* \* \* \*